(12) United States Patent
Shen et al.

(10) Patent No.: US 9,637,782 B2
(45) Date of Patent: May 2, 2017

(54) CHARGED TRIPLET-STATE QUENCHERS FOR MITIGATION OF PHOTO-INDUCED DAMAGE

(71) Applicant: Pacific Biosciences of California, Inc., Menlo Park, CA (US)

(72) Inventors: Gene Shen, Santa Clara, CA (US); Andrei Fedorov, San Bruno, CA (US); Wei-Chuan Sun, Mountain View, CA (US); Stephen Yue, Eugene, OR (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 741 days.

(21) Appl. No.: 14/039,397

(22) Filed: Sep. 27, 2013

(65) Prior Publication Data

US 2014/0093935 A1 Apr. 3, 2014

Related U.S. Application Data

(60) Provisional application No. 61/707,621, filed on Sep. 28, 2012.

(51) Int. Cl.
*C12Q 1/68* (2006.01)
*C12N 9/96* (2006.01)

(52) U.S. Cl.
CPC ............ *C12Q 1/6869* (2013.01); *C12N 9/96* (2013.01); *C12Q 2527/127* (2013.01)

(58) Field of Classification Search
CPC ................ C12Q 1/6869; C12Q 2527/127
USPC ............................................ 435/6.1; 536/23.1
See application file for complete search history.

(56) References Cited

U.S. PATENT DOCUMENTS

| 7,056,661 | B2 | 6/2006 | Korlach et al. |
| 7,211,414 | B2 | 5/2007 | Hardin et al. |
| 7,476,503 | B2 | 1/2009 | Turner et al. |
| 7,767,394 | B2 | 8/2010 | Turner et al. |
| 7,993,895 | B2 | 8/2011 | Eid et al. |
| 7,998,717 | B2 | 8/2011 | Eid et al. |
| 8,071,346 | B2 | 12/2011 | Eid et al. |
| 8,198,023 | B2 | 6/2012 | Ma et al. |
| 8,252,911 | B2 | 8/2012 | Bjornson et al. |
| 8,388,982 | B2 | 3/2013 | Kong et al. |
| 8,501,922 | B2 | 8/2013 | Otto et al. |
| 2008/0241892 | A1 | 10/2008 | Roitman et al. |
| 2010/0003765 | A1 | 1/2010 | Dixon et al. |
| 2010/0047802 | A1 | 2/2010 | Bjorson et al. |
| 2012/0009567 | A1 | 1/2012 | Fedorov et al. |
| 2012/0052488 | A1 | 3/2012 | Yue et al. |
| 2014/0038178 | A1* | 2/2014 | Otto ............... C07H 21/00 435/6.1 |

OTHER PUBLICATIONS

Eid et al., "Real-Time DNA Sequencing From Single Polymerase Molecules," Science (2009) 323:133-138.
Levene et al., "Zero-mode Waveguides for Single-molecule Analysis at High Concentration" Science (2003) 299:682-686.
Lopez et al., "Use of p-nitrobenzyloxycarbonyl (pNZ) as a permanentprotecting group in the synthesis of Kahalalide F analogs," Tetrahedron Letters 46:7737-7741. 2005.

* cited by examiner

*Primary Examiner* — Jezia Riley
(74) *Attorney, Agent, or Firm* — David C. Scherer; Deana A. Arnold

(57) ABSTRACT

Mitigation of photo-induced damage in excitation illuminated reactions and analyses utilizing such reactions results in an enhanced performance for the reactions and the analyses. There is provided a novel class of triplet-state quenchers for mitigating photo-induced damage which are both simple in structure and effective at preventing and/or reducing photo-induced damage to reaction components of excitation illuminated reaction mixtures. Also provided are methods of using the compounds of the invention, devices and kits incorporating the compounds of the invention.

25 Claims, 15 Drawing Sheets

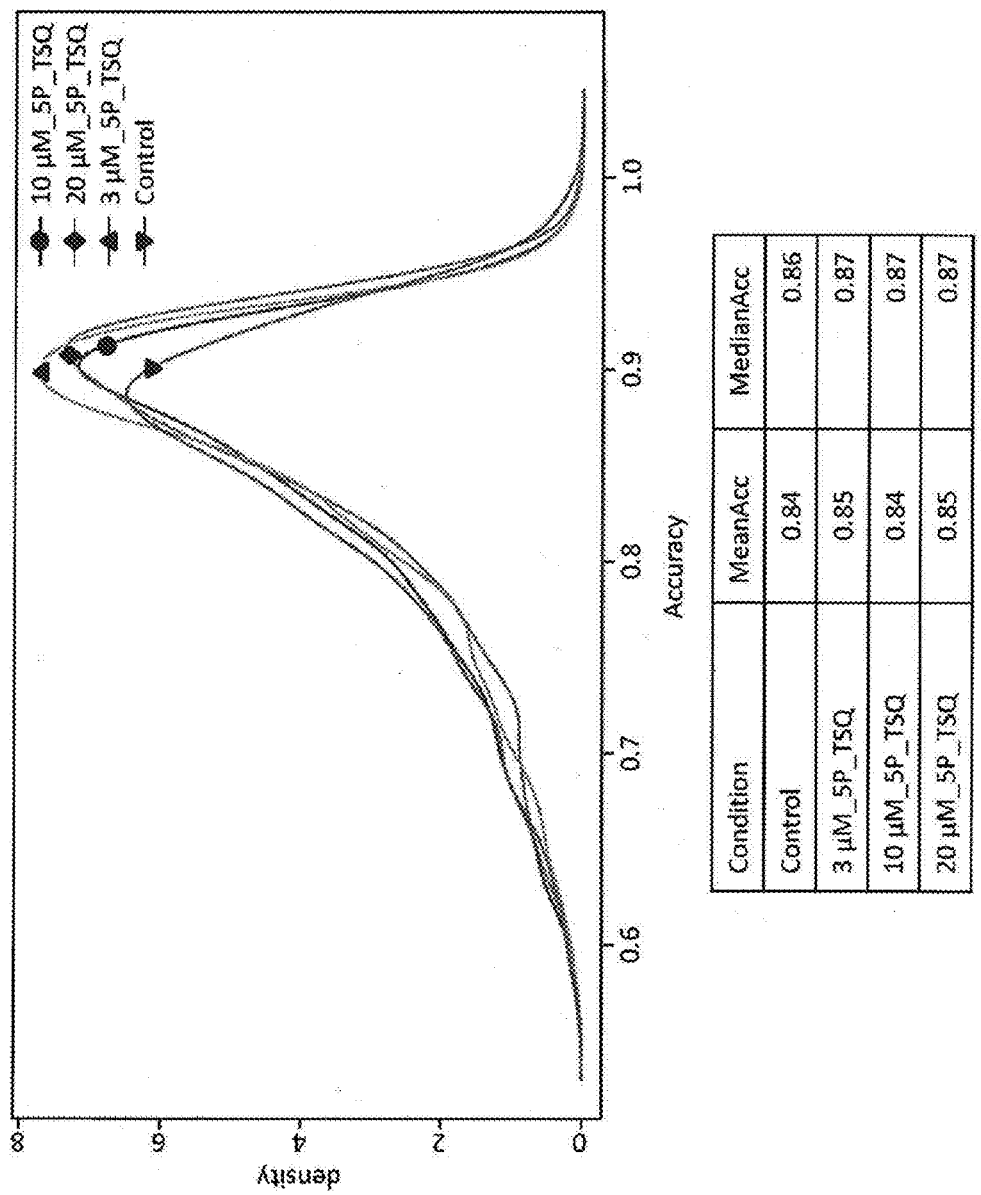

CHARGED TRIPLET-STATE QUENCHERS FOR MITIGATION OF PHOTO-INDUCED DAMAGE

CROSS-REFERENCE TO RELATED APPLICATIONS

This application claims the benefit of U.S. Provisional Application No. 61/707,621, filed Sep. 28, 2012, the disclosure of which is incorporated herein by reference in its entireties for all purposes.

STATEMENT REGARDING FEDERALLY SPONSORED RESEARCH

Not applicable.

BACKGROUND OF THE INVENTION

The use of optically detectable labeling groups, and particularly those groups having high quantum yields, e.g., fluorescent or chemiluminescent groups, is ubiquitous throughout the fields of analytical chemistry, biochemistry and biology. In particular, by providing a highly visible signal associated with a given reaction, one can better monitor that reaction as well as any potential effectors of that reaction. Such analyses are the basic tools of life science research in genomics, diagnostics, pharmaceutical research, and related fields.

To date, such analyses have generally been performed under conditions where the amounts of reactants are so far in excess that any adverse effects on the optical event are unnoticed. For example, such analyses based upon fluorescent labeling groups generally require the use of an excitation radiation source, e.g., a light source, directed at the reaction mixture, to excite the fluorescent labeling group, which is then separately detectable. However, prolonged exposure of chemical and biochemical reactants to such light sources, alone, or when in the presence of other components, e.g., the fluorescent groups, can lead, potentially, to damage to such reactants, e.g., proteins, enzymes, substrates, or the like.

Fluorescence is the result of a three-stage-process that occurs in the fluorophores or fluorescent dyes. The three-stage process includes: 1) excitation in which a photon with quantized energy from an external light source with certain wavelength is supplied and absorbed by the fluorophore, creating an excited electronic singlet state (S1'); 2) excited-state lifetime, during which the excited fluorophore undergoes several different changes to relax its energy to the lowest singlet state (S1); and 3) fluorescence emission in which a photon of energy (S1-S0) is emitted returning the fluorophore to its ground state.

One of the many pathways that dissipate the energy of the excited electronic singlet state is the intersystem crossing (ISC), involving a change in spin multiplicity, transiting the electron from S1 to the excited triplet state (T1). In many fluorescent dye molecules the formation of the much longer life-time triplet-state species greatly reduced the brightness of the fluorescence emission. In addition, it exhibits a high degree of chemical reactivity in this state, which often results in photobleaching and the production of damaging free radicals.

As noted previously, however, conventional formats for such reactions generally prevent any such effects from being problematic, or even being noticed.

A variety of analytical techniques are being explored, however, that deviate from previous formats, such that detrimental effects of such photo-induced damage have a more dramatic impact on the operation of the given analysis. In particular, real-time analyses of reactions that include fluorescent reagents can expose multiple different components to optical energy. Additionally, reactions based upon increasingly smaller amounts of reagents, e.g., in microfluidic or nanofluidic reaction vessels or channels, or in "single molecule" analyses, are more severely impacted by such damage. As such, the present invention is directed at methods and compositions that prevent or mitigate to some extent, the adverse effects of such photo-induced damage, and also to processes that benefit from such methods and/or compositions, among other useful processes and compositions.

BRIEF SUMMARY OF THE INVENTION

The present invention is generally directed to compositions, devices, systems and methods for reducing and/or eliminating photo-induced damage and its effects in illuminated reactions, and particularly those that utilize fluorescent and/or fluorogenic reactants.

In an exemplary embodiment, the invention provides a compound according to Formula I:

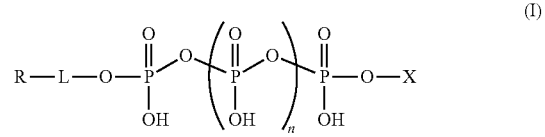

wherein R is a photoprotective moiety and the compound as a whole is a photoprotective agent. The index n is an integer selected from 1, 2, 3, 4, 5 and 6. The symbol X represents H or L'-R'. L and L' are independently selected linker moieties. In an exemplary embodiment, R' is a photoprotective moiety, which may or may not be structurally identical to R. In certain preferred embodiments, the symbol R' represents a substituted or unsubstituted aryl moiety.

In various embodiments, there is provided a reaction mixture including a first reactant and a second reactant comprising a fluorescent or fluorogenic molecule, and an additive according to Formula I. In an exemplary embodiment, in the absence of the additive, the interaction of the first and second reactants under excitation (e.g., illumination) causes photo-induced damage of the first reactant. The presence of the additive in the reaction mixture mitigates (e.g., reduces or prevents) the photo-induced damage of the first reactant.

In various embodiments, the first reactant is a biomolecule, e.g., a nucleic acid or protein, e.g., an enzyme.

In an exemplary embodiment, the invention provides a method for protecting an enzyme from photo-induced damage in an illuminated reaction. An illustrative method includes querying the reaction mixture by illuminating it and detecting a signal from a fluorescent or fluorogenic reagent in the reaction mixture. In this embodiment, the reaction mixture includes the enzyme, and a fluorescent or fluorogenic substrate for the enzyme, which, upon illumination produces a detectable signal. The reaction mixture also includes an additive according to Formula I. The photoprotective additive reduces the amount of photo-induced damage to the enzyme resulting from interaction of the enzyme with the fluorescent or fluorogenic substrate under the excitation illumination to an amount that is less than that which would occur in the absence of the photoprotective compound according to Formula I.

The invention also provides methods of performing a reaction under excitation illumination, comprising providing a substrate having a reaction mixture disposed thereon, wherein the reaction mixture comprises a first reactant, a second reactant and a photoprotective agent according to Formula I. The reaction mixture is illuminated on the substrate with excitation illumination. The photoprotective agent reduces the amount of photo-induced damage to the first reactant resulting from interaction of the first reactant with the second reactant under excitation illumination that would occur in the absence of the photo-induced damage mitigating agent.

In various embodiments, the invention provides methods of performing an enzyme reaction. In these embodiments, an enzyme in an observation region is contacted with a fluorescent or fluorogenic substrate for the enzyme and an additive according to Formula I. Excitation radiation is directed at and signals are detected from the observation region for a period that is less than a photo-induced damage threshold period. In various embodiments, compounds of the invention increases the photo-induced damage threshold period of the reaction mixture relative to this period in the absence of compounds of the invention.

In similar embodiments, the invention provides methods of monitoring a base extension reaction, comprising contacting a polymerase within an observation region with at least a first fluorescent or fluorogenic nucleotide analog and a photoprotective agent according to Formula I, and monitoring a fluorescent signal emitted from the observation region in response to illumination with excitation illumination. In various embodiments, the monitoring is for a period that is less than a photo-induced damage threshold period.

Also provided is a kit for mitigating photo-induced damage while performing a reaction with a fluorescent or fluorogenic substrate for an enzyme in the presence of the enzyme. The kit includes a photoprotective agent according to Formula I and one or more reactants for the reaction, e.g., the enzyme and/or the fluorogenic substrate.

The invention also provides devices that comprise a substrate having an observation region appropriate for performing an excitation illuminated reaction. In various embodiments, one or more reaction components, e.g., an enzyme, is immobilized within the observation region. A fluorescent or fluorogenic substrate for the enzyme and a photoprotective agent according to Formula I are disposed within the observation region.

Other objects, embodiments and advantages of the present invention are set forth in the detailed description that follows.

BRIEF DESCRIPTION OF THE DRAWINGS

FIG. 5C is a graph showing the effect of (TSQ)2-5P on accuracy (Acc) in a single molecule nucleic acid analysis.

DETAILED DESCRIPTION OF THE INVENTION

Introduction

Figure 1A:
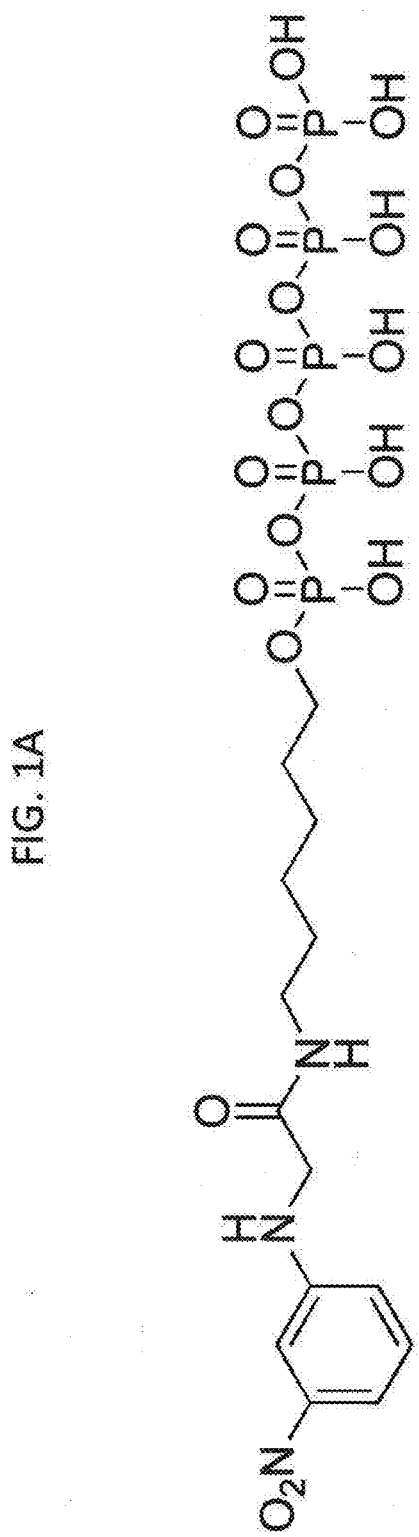
FIG. 1A is a formula of an exemplary photoprotective agent of the invention.

Various embodiments of the present invention are generally directed to photoprotective compounds and methods of performing improved illuminated reactions using these compounds, and particularly reactions that employ fluorescent or fluorogenic reactants. The compositions and methods of the invention are useful to mitigate the effects of and/or reduce photo-induced damage to one or more of the various reactants present in such reactions. The invention includes compounds, compositions, devices, kits and methods for preventing or reducing such photo-induced damage as well as methods for mitigating the impact such photo-induced damage might have on an overall analysis.

In various embodiments, the present invention is directed to photoprotective compositions, and methods and devices utilizing such compounds, that reduce the amount of photo-induced damage to one or more fluorescent or non-fluorescent reactants during excitation illumination, e.g., with an excitation radiation source. In particular, compositions are provided that yield a reduction in the level of photo-induced damage (and/or an increase in the photo-induced damage threshold period) as compared to such reactions in the absence of such compositions. As used herein, the components of such compositions that provide such effects are generally referred to interchangeably as photoprotective agents or photo-induced damage mitigating agents. In particular, photoprotective agents are provided in the context of the analytical reaction to reduce the level of photo-induced damage (and/or increase the photo-induced damage threshold period), that would otherwise have occurred but for the presence of the photoprotective agents.

The invention is generally applicable to any of a variety of optical assays that require illumination from a moderate to high fluence source and/or photoactivated conversion or excitation of chemical groups, e.g., fluorophores. In various embodiments, the invention is a component of analyses that utilize very limited concentrations of reactants that might be subject to photo-induced damage. As will be appreciated, in such reagent-limited analyses, any degradation of a critical reagent will dramatically impact the analysis, by further limiting the reagent. Certain preferred examples of optical assays that find particular benefit from the compounds and methods provided herein are described in various publications including, but are not limited to, U.S. Pat. Nos. 7,315,019, 7,056,661, 6,917,726, 8,143,030, and 8,153,375, and U.S. Patent Publication No. 2011/0183320.

One particularly apt example of analysis benefiting from the invention are single molecule biological analyses, including, inter alia, single-molecule, nucleic-acid sequencing analyses; single-molecule enzyme analyses; and hybridization assays, e.g., antibody assays, nucleic acid hybridization assays, and the like, where the reagents of primary import are subjected to prolonged illumination with relatively concentrated light sources, e.g., lasers or other concentrated light sources, e.g., mercury, xenon, halogen or other lamps, in an environment where photoconversion/excitation is occurring, with its associated generation of products. For example, in an analytical reaction that monitors a single reaction component, e.g., a single enzyme, damage to that component that alters or prevents the reaction from proceeding shortens the length of time the reaction can be monitored. By mitigating that damage, the analytical reaction is protected and, therefore, can proceed for a longer period of time, thereby allowing more reaction data to be collected than without such protection.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

Definitions

Where chemical moieties are specified by their conventional chemical formulae, written from left to right, they optionally equally encompass the moiety which would result from writing the structure from right to left, e.g., —CH$_2$O— is intended to also recite —OCH$_2$—; —NHS(O)$_2$— is also intended to optionally represent. —S(O)$_2$HN—, etc. Moreover, where compounds can be represented as free acids or free bases or salts thereof, the representation of a particular form, e.g., carboxylic or sulfonic acid, also discloses the other form, e.g., the deprotonated salt form, e.g., the carboxylate or sulfonate salt. Appropriate counterions for salts are well-known in the art, and the choice of a particular counterion for a salt of the invention is well within the abilities of those of skill in the art. Similarly, where the salt is disclosed, this structure also discloses the compound in a free acid or free base form. Methods of making salts and free acids and free bases are well-known in the art.

"Cyanine," as used herein, refers to aryl and heteroaryl polymethine dyes such as those based upon the cyanine, merocyanine, styryl and oxonol ring.

As used herein, "nucleic acid" means any natural or non-natural nucleoside, or nucleotide and oligomers and polymers thereof, e.g., DNA, RNA, single-stranded, double-stranded, triple-stranded or more highly aggregated hybridization motifs, and any chemical modifications, analogs, and mimetics thereof. Modifications include, but are not limited to, conjugation into a compound of the invention. Further modifications include those providing the nucleic acid with a group that incorporates additional charge, polarizability, hydrogen bonding, electrostatic interaction, fluxionality or functionality to the nucleic acid. Exemplary modifications include the attachment to the nucleic acid, at any position, of one or more hydrophobic or hydrophilic moieties, minor groove binders, intercalating agents, quenchers, chelating agents, metal chelates, solid supports, and other groups that are usefully attached to nucleic acids. Exemplary nucleic acids of the invention include one or more dye moiety of the invention bound thereto.

Exemplary modified nucleic acids include, but are not limited to and may comprise combinations of, locked nucleic acids (LNAs), peptide nucleic acids (PNAs), those with phosphodiester group modifications (e.g., replacement of O$^-$ with OR, NR, or SR), 2'-, 3'-and 5'-position sugar modifications, modifications to the nucleobase moiety, e.g., 5-position pyrimidine modifications, 8-position purine modifications, modifications at exocyclic amines, substitution of 4-thiouridine, substitution of 5-bromo or 5-iodouracil; backbone modifications, i.e., substitution of P(O)O$_3$ with another moiety, methylations, hydroxylations, unusual base-pairing combinations such as the isobases, isocytidine and isoguanidine and the like. Nucleic acids can also include noncanonical or non-natural bases, e.g., nitroindole. Non-natural nucleobases include bases that are modified with a compound of the invention or a linker-compound of the invention construct, a minor groove binder, an intercalating agent, a hybridization enhancer, a chelating agent, a metal chelate, a quencher, a fluorophore, a fluorogenic compound, etc. Modifications within the scope of "nucleic acid" also include 3' and 5' modifications with one or more of the species described above.

An analytical reaction may comprise more than one type of nucleic acid. For example, a polymerase-mediated, sequencing-by-synthesis reaction typically comprises a template nucleic acid, a primer oligonucleotide, nucleotides (or analogs thereof), and a nascent strand produced by the polymerase by incorporation of bases of the nucleotides (or analogs thereof). The template may comprise a polynucleotide derived from a sample, as well as nucleic acid adapter sequences that facilitate amplification and/or sequencing of the template.

The nucleic acid can comprise DNA, RNA or chimeric mixtures or derivatives or modified versions thereof. Nucleic acids, e.g. probes and/or template nucleic acids, can be present as a single strand, duplex, triplex, etc. Moreover, as discussed above, the nucleic acid can be modified at the nucleobase moiety, sugar moiety, or phosphate backbone with other groups including but not limited to radioactive labels, magnetic labels, minor groove binders, intercalating agents, methyl groups, hydroxymethyl groups, formyl groups, carboxyl groups, sugar groups, donor and/or acceptor moieties and the like.

In addition to the naturally occurring "nucleobases," adenine, cytosine, guanine and thymine, nucleic acid components of the compounds of the invention optionally include modified bases. These components can also include modified sugars. For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetyleytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N2-carboxypropyl) uracil, (acp3)w, nitroindole, and 2,6-diaminopurine. The dye of the invention or another probe component can be attached to the modified base.

In another embodiment, the nucleic acid comprises at least one modified sugar moiety selected from the group including, but not limited to, arabinose, 2-fluoroarabinose, xylulose, and hexose. The dye or another probe component can be attached to the modified sugar moiety.

In yet another embodiment, the nucleic acid comprises at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof. The dye or another probe component can be attached to the modified phosphate backbone. "Nucleic acid" also includes a component of a conjugate with one or more modified phosphate bridges (e.g., P(O)O$_3$) by conjugating a linker-dye conjugate of the invention to the nucleic acid, e.g., replacing or derivatizing an oxygen of the bridge, with a compound of the invention or a species that includes a compound of the invention attached to an adaptor. For example, "nucleic acid" also refers to species in which, rather than the P(O)(O$^-$)O$_2$ moiety of a naturally occurring nucleic acid, includes the moiety ROP(O)(O—)O, in which R is a dye-linker conjugate of the invention, an adaptor, a linker-adaptor cassette or a fluorescent dye-linker-adaptor cassette. An exemplary linker is an amino acid or peptide linker of the invention. Although certain preferred linkers of the invention are amino acid or peptide linkers, linkers of the invention are not limited to amino acid or peptide linkers, and can comprise or be composed of other types of molecules, e.g., polynucleotides. In various embodiments, one oxygen of this structure is bound to the phosphorus atom of a P(O)(O$^-$)O$_2$, such that the nucleic acid includes two or more phosphate moieties bound to each other.

Further exemplary nucleic acids of the invention include a nucleotide having a polyphosphate moiety, e.g., pyrophosphate or a higher homologue, such as the 3-mer, O-mer, 5-mer, 6-mer, 7-mer, 8-mer and the like. Exemplary nucleic acids include such a polyphosphate moiety bonded to the 5'-oxygen of a nucleoside. In addition to the attached polyphosphate moiety can include a modified phosphate bridge, such as those exemplified herein. In an exemplary embodiment, the modified phosphate bridge is modified with an adaptor, a linker dye conjugate, a linker-adaptor cassette or a fluorescent dye-linker-adaptor cassette. In an exemplary embodiment, the linker is an amino acid or peptide linker such as those set forth herein. In other embodiments, the linker is a polynucleotide linker. Examples of some nucleic acids finding use in the present invention are set forth in Published U.S. Patent Application Nos. 2003/0077610, 2003/0124576, 2003/0162213, 2004/0241716, 2007/0072196, 2009/0325260, 2010/00152424, 2010/0167299, and 2012/0052507, as well as U.S. Pat. Nos. 5,688,648, 6,399,335, 7,041,812, 7,056,661, 7,052,839, 7,223,541, 7,405,281, 7,777,013, 8,058,031, 7,968,702, 7,973,146, and 8,133,702, the full disclosures of which are incorporated herein by reference for all purposes.

Furthermore, "nucleic acid" includes those species in which one or more internucleotide bridge does not include phosphorus: the bridge being optionally modified with a compound of the invention or a linker-dye construct of the invention. An exemplary bridge includes a substituted or unsubstituted alkyl or substituted or unsubstituted heteroalkyl moiety in which a carbon atom is the locus for the interconnection of two nucleoside sugar residues (or linker moieties attached thereto) and a linker-dye construct of the invention. The discussion above is not limited to moieties that include a carbon atom as the point of attachment; the locus can also be another appropriate linking atom, such as nitrogen or another atom.

Phosphodiester linked nucleic acids of the invention can be synthesized by standard methods known in the art, e.g. by use of an automated DNA synthesizer using commercially available amidite chemistries (Ozaki et al., *Nucleic Acids Research,* 20: 5205-5214 (1992); Agrawal et al., *Nucleic Acids Research,* 18: 5419-5423 (1990); Beaucage et al., *Tetrahedron,* 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679). Nucleic acids bearing modified phosphodiester linking groups can be synthesized by methods known in the art. For example, phosphorothioate nucleic acids may be synthesized by the method of Stein et al. (*Nucl. Acids Res.* 16:3209 (1988)), methylphosphonate nucleic acids can be prepared by use of controlled pore glass polymer supports (Sarin et al., *Proc. Natl. Acad. Sci. U.S.A.* 85:7448-7451 (1988)). Other methods of synthesizing both phosphodiester-and modified phosphodiester-linked nucleic acids will be apparent to those of skill in the art.

As will be appreciated, the photo-induced damage sought to be prevented by the methods and compositions of the invention includes photo-induced damage to fluorescent or fluorogenic reagents, e.g., photobleaching, as well as prevention or reduction of downstream photo-induced damage to other reagents. For example, where an analysis monitors the activity of reactive proteins or enzymes, photo-induced damage of these reaction components can cause changes in the progress or fidelity of the reaction, and these changes perturb the results (e.g., data, product, kinetics, etc.) of the reaction. Without being bound to a theory of operation, such photo-induced damage may include damage to enzymes or reactive proteins, or irreversible interactions between such enzymes or proteins and excited fluorescent or fluorogenic moieties in the reaction mixture. As suggested by the foregoing, photo-induced damage generally refers to an alteration in a given reagent, reactant or the like, that causes such reagent to have altered functionality in a desired reaction, e.g., reduced fluorescence, reduced activity, reduced specificity, or a reduced ability to be acted upon, converted, or modified, by another molecule, that results from, either directly or indirectly, a photo-induced reaction. In exemplary embodiments, a photo-induced reaction triggered by illumination of a reaction mixture creates a damaged reactant that interacts with and causes damage to one or more other reactants. Typically, such a photo-induced reaction directly impacts either the reactant of interest, e.g., direct photo-induced damage, or impacts a reactant within one, two or three reactive steps of such reactant of interest. For example, exposure of a fluorescent dye to excitation illumination can cause the dye to convert to triplet state, and since triplet-state fluorophores are highly reactive, they can cause damage to other components of the reaction mixture, e.g., proteins/enzymes, nucleic acids, etc. For ease of discussion, the detrimental impact of the photo-induced damage event, whether resulting from actual damage to a given reagent or from interaction with a damaged reagent, is generally referred to herein as photo-induced damage.

Of particular interest is the protection of reaction components that are of limited quantity in a reaction mixture, since their limited presence is more greatly impacted by even slight losses due to photo-induced damage. For example, in single-molecule analysis, loss of the single molecule, e.g., through photo-induced damage, effectively and prematurely ends the reaction. As generally referred to herein, such limited quantity reagents or reactants may be present in solution, but at very limited concentrations, e.g., less than 200 nM, in some cases less than 10 nM and in still other cases, less than 10 pM. In certain preferred embodiments, a limited quantity reagent or reactant is present as a single molecule being independently monitored during the course of an analytical reaction. In illustrative embodiments, however, such limited quantity reagents or reactants refer to reactants that are immobilized, or otherwise confined within a given area, so as to provide limited quantity of reagents in that given area, and in certain cases, provide small numbers of molecules of such reagents within that given area, e.g., from 1 to 1000 individual molecules, preferably between 1 and 10 molecules. For example, a limited quantity reagent may be a single immobilized enzyme acting on substrates that are suspended in a reaction mixture, e.g., free in solution. As will be appreciated, photo-induced damage of immobilized reactants at a given reaction site or observation area will have a substantial impact on the reactivity of that area, as other, non-damaged reactants are not free to diffuse into, and mask the damage effects.

As used herein, "photoprotective agent," "photoprotective compound," "photoprotective additive," and "photo-induced damage mitigating agent" are used interchangeably and refer to any agent of the invention that acts to reduce or prevent damage to a reaction component that is directly or indirectly caused by exposure to illumination. A "photoprotective moiety" of the photoprotective agent is the portion of the photoprotective agent that serves to reduce or prevent the photo-induced damage to reaction components in an analytical reaction. In preferred embodiments, such illumination is of an intensity and wavelength appropriate for excitation of a fluorescent or fluorogenic moiety in the reaction mixture, e.g., "excitation illumination." In preferred embodiments, a photoprotective agent (a) prevents or reduces transition of a compound to a triplet state, and/or (b) shortens the lifetime of an excited compound in a triplet state, thereby reducing the amount of time the triplet-state compound can cause photo-induced damage to a reaction component. A photoprotective agent can attenuate, at least partly, the energy (e.g., light) emitted by a fluorescent dye, or otherwise alter the fluorescent properties of a fluorescent molecule relative to the fluorescent properties of the molecule in the absence of the photoprotective agent. Properties of fluorophores include, without limitation, intensity, excitation wavelength, emission wavelength, solubility in a reaction mixture, stability of fluorescence (e.g., "blinkiness"), lifetime in a particular energy state (e.g., triplet state), affinity for another reaction mixture component (e.g., an enzyme), size, hydrodynamic ratio, charge and the like. Such properties affect the fluorescence-based data collected during the assay, thus, the property affected can vary between assay formats. An exemplary mode of altering the fluorescent properties of a fluorescent molecule is through energy transfer between the fluorescent molecule and a photoprotective moiety of a photoprotective agent. Exemplary photoprotective moieties include triplet-state quenchers (e.g., cyclooctatetraene or cycloheptatriene), reducing agents, singlet oxygen quenchers, and others provided in the art, e.g., in U.S. Pat. Nos. 7,998,717 and 7,993,895, and U.S. Patent Publications 2012/0052488 and 2010/0136592.

As used herein, the amount of time an illuminated analysis may be carried out before photo-induced damage so significantly impacts one or more reactants to render the analysis non-useful, is referred to as the "photo-induced damage threshold period", or "PID threshold". The PID threshold can be measured as a duration of an illuminated analysis during which useful data can be collected from an analytical reaction before the occurrence of sufficient photo-induced damage to severely perturb or terminate the reaction. In general, the PID threshold for a given analytical reaction is determined empirically by performing the reaction in the presence of illumination and measuring the amount of time the reaction can proceed under illumination before the detrimental effects of photo-induced damage are detectable and/or sufficient to negatively affect the analysis. The same reaction can be performed in the absence of illumination to provide a negative control for the effects of illumination on the reaction. Although a PID threshold can be determined for a single reaction, e.g., during the course of the reaction, PID thresholds are typically determined based on an average duration of a set of identical reactions. The average value is applicable to other reactions carried out under the same conditions as the set of reactions used to determine the average. Addition of a photoprotective agent serves to extend the PID threshold so the duration of the reaction is extended allowing reaction data unperturbed by photo-induced damage to be collected over a longer period. This allows for greater efficiencies in performance of such reaction since fewer reactions are required to generate an equivalent amount of data when each reaction can be extended.

Although the PID threshold is a temporal metric, various non-temporal proxies can be used to detect an increase in the PID threshold. For example, an increase in product from a reaction can serve as a proxy for the duration of the reaction. In certain embodiments that comprise synthesis of a polymer product (e.g., polynucleotide or polypeptide synthesis), the length of the polymer produced can be taken as an indirect measure of the PID threshold. Similarly, where the data generated can be appropriately quantified, the generation of "more" data can serve as a proxy for the duration of the reaction. For example, for a nucleic acid sequencing reaction, the length of the sequence generated ("read length") can be used as an indirect measure of the PID threshold. Yet further, kinetic metrics of a reaction can also be used to determine a PID threshold for a reaction, e.g., where a particular kinetic measure serves as a surrogate threshold. For example, one or more kinetic metrics of an ongoing reaction can be used to determine when sufficient photo-induced damage as occurred so as to render unreliable the data being generated. This surrogate threshold can be based upon various kinetic parameters including, without limitation, rate of catalysis, rate of binding, rate of translocation, frequency of pausing, fidelity (e.g., error rate), and the like. For example, for a given analytical reaction the PID threshold may be defined as the point during the reaction at which the rate of the subject reaction is reduced by at least 20% over the same reaction in the absence of such illumination, e.g., more than 50%, e.g., more than 90%.

The term "alkyl," by itself or as part of another substituent, means, unless otherwise stated, a straight or branched chain, or cyclic hydrocarbon radical, or combination thereof, which may be fully saturated, mono-or polyunsaturated and can include mono-, di-and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1-and 3-propynyl, 3-butynyl, and the higher homologs and isomers. The term "alkyl," unless otherwise noted, includes "alkylene" and, optionally, those derivatives of alkyl defined in more detail below, such as "heteroalkyl."

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P and S, and wherein the nitrogen and sulfur atoms may optionally be oxidized and the nitrogen heteroatom may optionally be quaternized. The heteroatom(s) O, N, S, P and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di-and multivalent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di-and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) optionally refers to both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =N—OR', —NR'R", —SR', -halogen, —SiR'R"R"', —OC(O)R', —C(O)R', —CO$_2$R', —CONR'R", —OC(O)NR'R", —NR"C(O)R', SO$_3$R', —NR'—C(O)NR"R"', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The substituents set forth in the paragraph above are referred to herein as "alkyl group substituents."

Similar to the substituents described for the alkyl radical, substituents for the aryl and heteroaryl groups are varied and are selected from, for example: halogen, —OR', =O, =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R' SO$_3$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R"" are preferably independently selected from hydrogen, (C$_1$-C$_8$) alkyl and heteroalkyl, unsubstituted aryl and heteroaryl, (unsubstituted aryl)-(C$_1$-C$_4$)alkyl, and (unsubstituted aryl) oxy-(C$_1$-C$_4$)alkyl. When a compound of the invention includes more than one R group, for example, each of the R groups is independently selected as are each R', R", R''' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

The substituents set forth in the two paragraphs above are referred to herein as "aryl group substituents."

The term, "reaction mixture," refers to a mixture that includes one or more analytes of interest to be analyzed, e.g., qualitatively or quantitatively, using a material, process, or device of the present invention. Examples of such analytes include, without limitation, biomolecules (e.g., nucleic acids, proteins, polysaccharides, lipids, etc.) and bioactive agents (e.g., drugs, pesticides, herbicides, etc.). A reaction mixture also includes other components, for example, diluents, buffers, detergents, and contaminating species, debris and the like, often from the same source as the analyte. Illustrative examples of sources for analytes include urine, sera, blood plasma, total blood, saliva, tear fluid, bile, biopsies, buccal samples, cerebrospinal fluid, mucus, body tissues, cells, and the like. In various embodiments, a reaction mixture includes a photoprotective agent of the invention.

"Excitation illumination" as used herein refers to illumination of an intensity and wavelength sufficient to cause a detectable change of energy in a component of a reaction mixture, e.g., resulting in emission of energy. An example of "excitation illumination" is illumination utilized to excite a fluorophore such that it absorbs the illumination and emits fluorescence, e.g., visible light.

In various embodiments, one or more component of a photoprotective agent is substituted with poly(ethylene glycol). The term PEG or poly(ethylene glycol) is intended to be inclusive and not exclusive. The term PEG includes poly(ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG with degradable linkages therein.

The PEG can be linear or branched. Branched PEGs are generally known in the art. Typically, a branched PEG has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)$_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as a component of the compounds according to Formula I and/or Formula II.

The Embodiments

Compounds

In an exemplary embodiment, the invention provides a photoprotective compound that includes one or more photoprotective moieties linked to a charged moiety, e.g., including multiple negative charges, which also can be referred to as an "oligo-anion moiety" or a "poly-anion moiety." Exemplary charged moieties include poly(amino acids), poly(phosphates), poly(sulfonates), poly(arsonates), poly(phosphonates), and poly(carboxylic acids). The one or more photoprotective moiety is conjugated to the charged moiety by one or more zero-or higher-order linker, which can comprise aryl portions, alkyl portions, or a combination thereof.

Without being bound to a particular theory or mechanism of operation, it is believed that the charged moiety serves as a "delivery vehicles" to bring moieties linked thereto, e.g., photoprotective moieties such as triplet-state quenchers, in close proximity to a reaction component susceptible to photo-induced damage, for example, an enzyme (e.g., a polymerase, nuclease, helicase, ligase, topoisomerase, kinase, and the like) to provide an increased "local" concentration of the photoprotective moiety around the susceptible reaction component, e.g., an enzyme or other reactive component. This increase in local concentration allows the practitioner to use significantly less of the photoprotective compound than would be required for an additive lacking the charged moiety to achieve an equivalent amount of protection from photo-induced damage. For example, in certain preferred embodiments the molar concentration of a photoprotective compound of the invention that is sufficient for prevention or reduction of photo-induced damage is less than 10%, 5%, 3%, 2%, 1%, 0.5%, 0.3%, or 0.25% of the molar concentration of a photoprotective additive lacking the charged moiety needed to achieve the same level of mitigation of photo-induced damage. This drastic decrease in the molar concentration of a photoprotective additive was unexpected and one of ordinary skill will recognize the usefulness of such compounds in illuminated reactions that encompass not only those exemplary illuminated reactions described herein, but also other illuminated reactions in which it is beneficial to reduce or prevent photo-induced damage to reaction components.

In various embodiments, the invention provides a photoprotective compound according to Formula I:

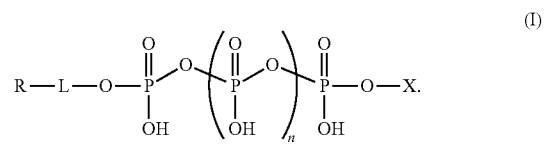

(I)

In Formula I, R is a photoprotective moiety. The index n is an integer selected from 1, 2, 3, 4, 5 and 6. The symbol X represents H or L'-R'. L and L' are independently selected linker moieties. The symbol R' represents a substituted or unsubstituted aryl moiety. In an exemplary embodiment, R' is a photoprotective moiety.

In various embodiments, the invention provides a photoprotective compound according to Formula II:

Y—R—L(COOH)$_m$    (II).

In Formula II, R is a photoprotective moiety. The symbol Y represents H or L'(COOH)$_{m'}$. The indexes m and m' are independently selected integers between 1 and 10, preferably selected from 2, 4, 6, and 8. L and L' are independently selected linker moieties.

For both Formula I and Formula II, L and L' are any zero-or higher-order linker. In exemplary embodiments, one or both of L and L' are or comprise alkyl moieties, optionally further substituted with one or more "alkyl group substituent" as that term is defined herein. In various embodiments, one or more of L and L' includes one or more methylene moieties. In certain embodiments, one or both of L and L' are or comprise aryl moieties. In some embodiments, one or both of L and L' are branched linkers. In various embodiments, one or both of L and L' are substituted with one or more carboxylic acid groups, e.g., 3, 4, 5 or 6 carboxylic acid groups.

In various embodiments, R' is a second photoprotective moiety, which is the same as or different from the first photoprotective moiety R. R' may also be a moiety that alters fluorescence intensity of the fluorophore or a property other than the fluorescence intensity of the fluorophore. For example, in one embodiment, R' is a moiety that stabilizes the fluorescence of the fluorophore and decreases the appearance of fluorophore blinkiness in an assay. In alternative embodiments, one or both of R or R'comprise multiple photoprotective moieties, e.g., attached to a linker having multiple attachment sites. Such multiple photoprotective agents can comprise multiple molecules of the same type of photoprotective moiety, or different types of photoprotective moieties.

Photoprotective moieties are generally known in the art and such moieties are of use in the compounds, compositions, methods and devices of the present invention. In an exemplary embodiment, the photoprotective moiety is a nitrobenzene moiety or includes a nitrobenzene moiety within its structure. Exemplary nitrobenzene moieties include a p-nitrobenzyl methylenecarbamate or a 3-nitrobenzamide. As will be appreciated by those of skill in the art, these exemplary moieties can be further substituted with other useful moieties. Further, the photoprotective moiety within the compound according to Formula I or Formula II can be charged or uncharged. In an exemplary embodiment, the photoprotective compound carries at least one or more positive or negative charges. In various embodiments, the photoprotective moiety is a triplet-state quencher. In alternative embodiments, the photoprotective moiety is a single-molecule ROXS. Specific examples of photoprotective compounds including single-molecule ROXS compounds are described in detail in U.S. Pat. Nos. 7,998,717 and 7,993,895, and U.S. Patent Publications 2012/0052488 and 2010/0136592. In an exemplary embodiment, the photoprotective moiety is a triplet-state quencher for an excited fluorophore used in a reaction or analysis in conjunction with the photoprotective agent of the invention.

In various embodiments, the moieties R and R' in compounds of the invention are independently selected moieties according to Formula III:

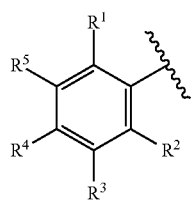

(III)

wherein $R^1$, $R^2$, $R^3$, $R^4$, and $R^5$ are independently members selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^6R^7$, $-NR^6R^7$, $-OR^6$, $-S(O)_2R^6$, $-C(O)R^6$, $-COOR^6$, $-CONR^6R^7$, $-S(O)_2OR^6$, $-OC(O)R^6$, $-C(O)NR^6R^7$, $-NR^6C(O)R^7$, $-NR^6SO_2R^7$ and $-NO_2$, wherein two or more of $R^1$, $R^2$, $R^3$, $R^4$ and $R^5$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl.

$R^6$ and $R^7$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^6$ and $R^7$, together with the atoms to which they are bonded, are optionally joined to form a 5-to 7-membered ring which is a member selected from substituted or unsubstituted cycloalkyl, substituted or unsubstituted heterocycloalkyl, substituted or unsubstituted aryl and substituted or unsubstituted heteroaryl.

In an exemplary embodiment, Formula III includes one or more PEG moieties attached thereto, either directly or through a linker.

In various embodiments, at least one R and/or R' moiety includes one or more $NO_2$ moiety at a position selected from $R^1$, $R^2$, $R^3$, $R^4$, and $R^5$.

In an exemplary embodiment, R and R' are each moieties independently selected from Formula IV:

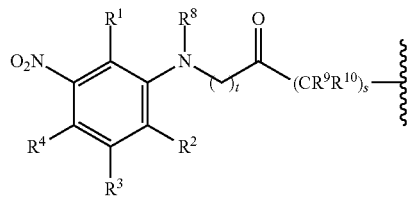

(IV)

wherein R' is H or substituted or unsubstituted alkyl. $R^9$ and $R^{10}$ are independently selected from H, substituted or unsubstituted alkyl, substituted or unsubstituted heteroalkyl, substituted or unsubstituted aryl, substituted or unsubstituted heteroaryl, halogen, CN, CF ac acyl, $-SO_2NR^{11}R^{12}$, $-NR^{11}R^{12}$, $-OR^{11}$, $-S(O)_2R^{11}$, $-C(O)R^{11}$, $-COOR^{11}$, $-CONR^{11}R^{12}$, $-S(O)_2OR^{11}$, $-C(O)NR^{11}R^{12}$, $-NR^{11}C(O)R^{12}$, $-NR^{11}SO_2R^{12}$ and $-NO_2$.

$R^{11}$ and $R^{12}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^6$ and $R^7$, together with the atoms to which they are bonded, are optionally joined to form a 5-to 7-membered ring which is a member selected from substituted or unsubstituted cycloalkyl, substituted or unsubstituted heterocycloalkyl, substituted or unsubstituted aryl and substituted or unsubstituted heteroaryl; and s and t are independently selected from 0, 1, 2, 3, 4, 5, 6; 7, 8, 9 and 10. When s is greater that 1, each $CR^9R^{10}$ is independently selected.

Figure 1B:
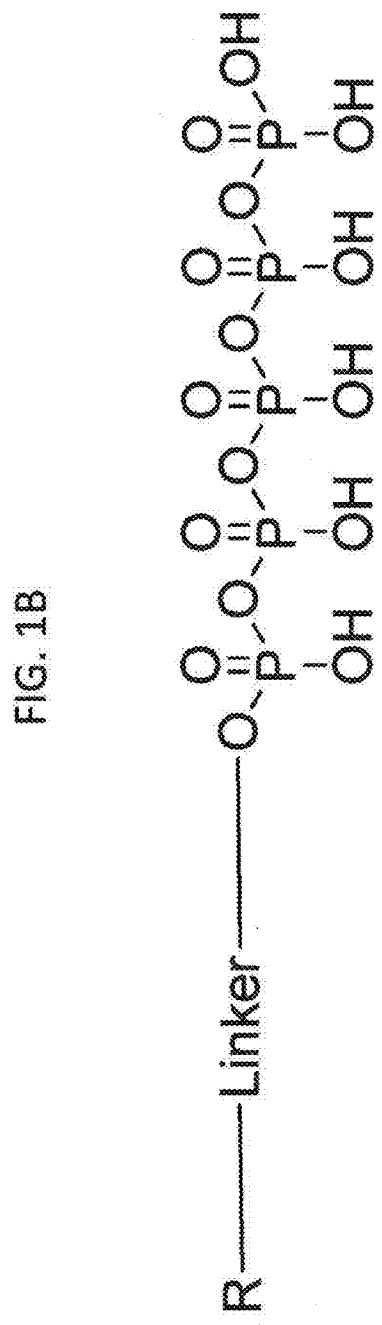
FIG. 1B is a generic formula for an exemplary photoprotective agent of the invention.
Figure 3:
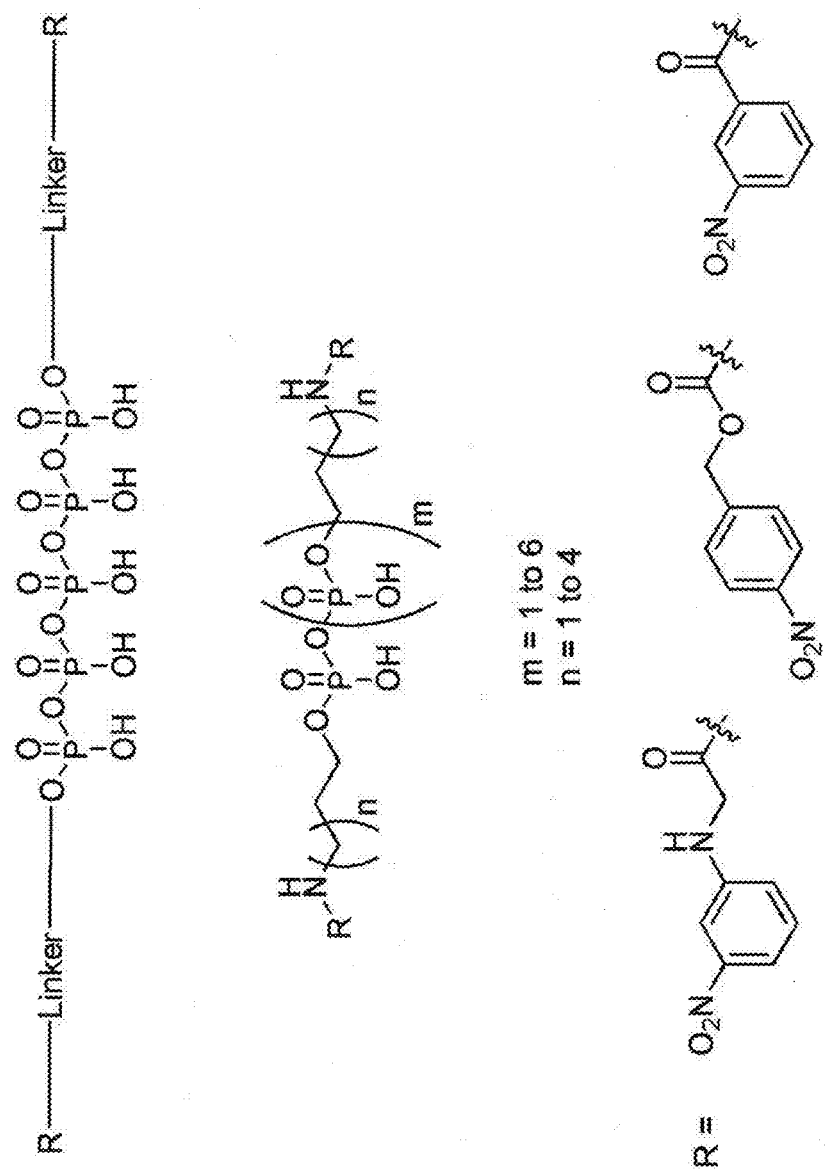
FIG. 3 shows exemplary formulae of compounds of the invention.
Figure 4A:
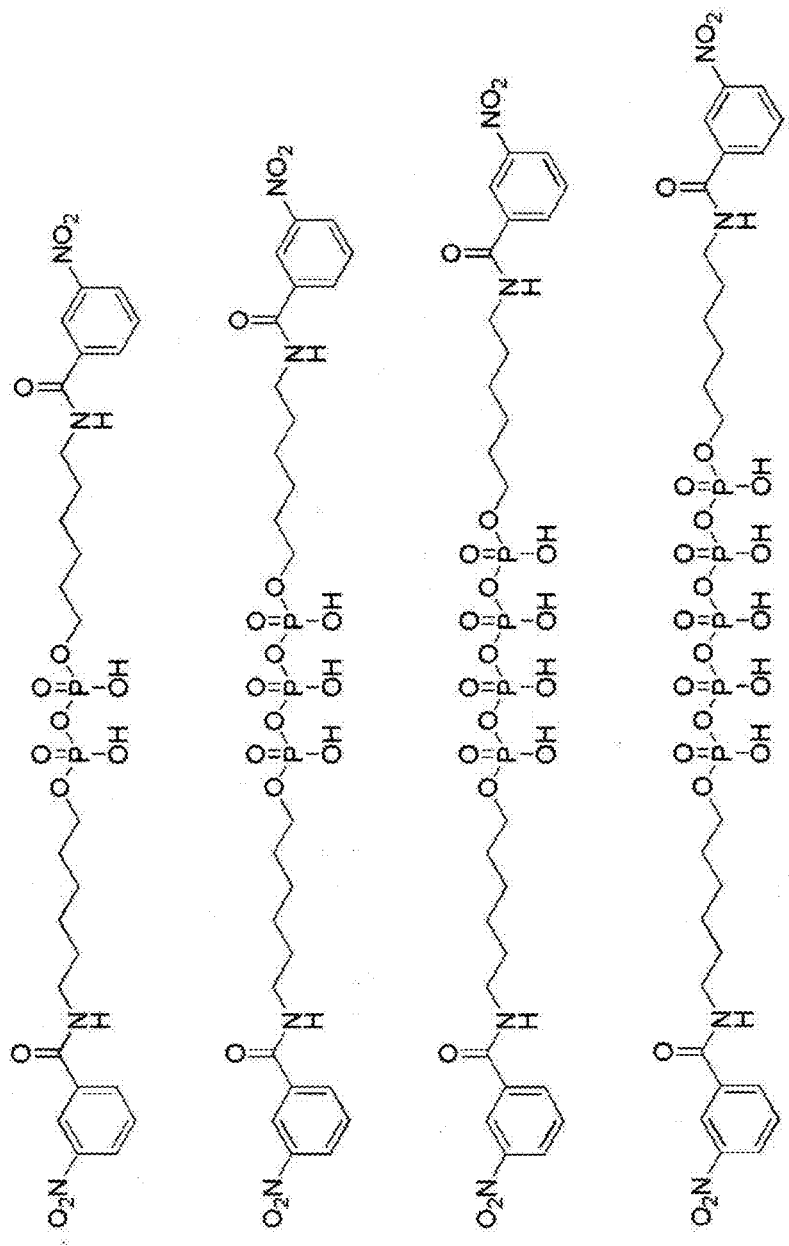
FIG. 4A-C provides a table showing exemplary compounds of the invention.
Figure 4B:
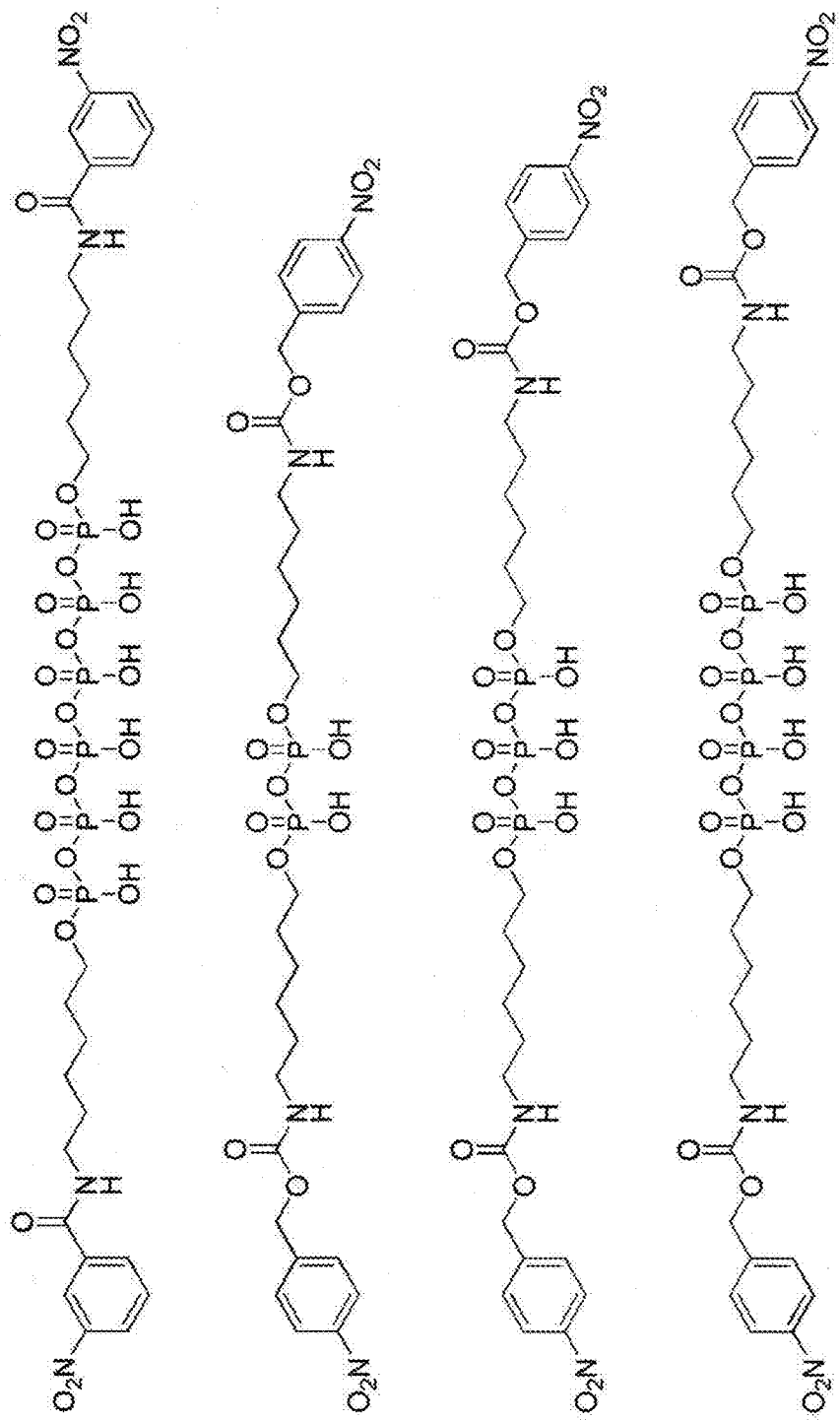
Figure 4C:
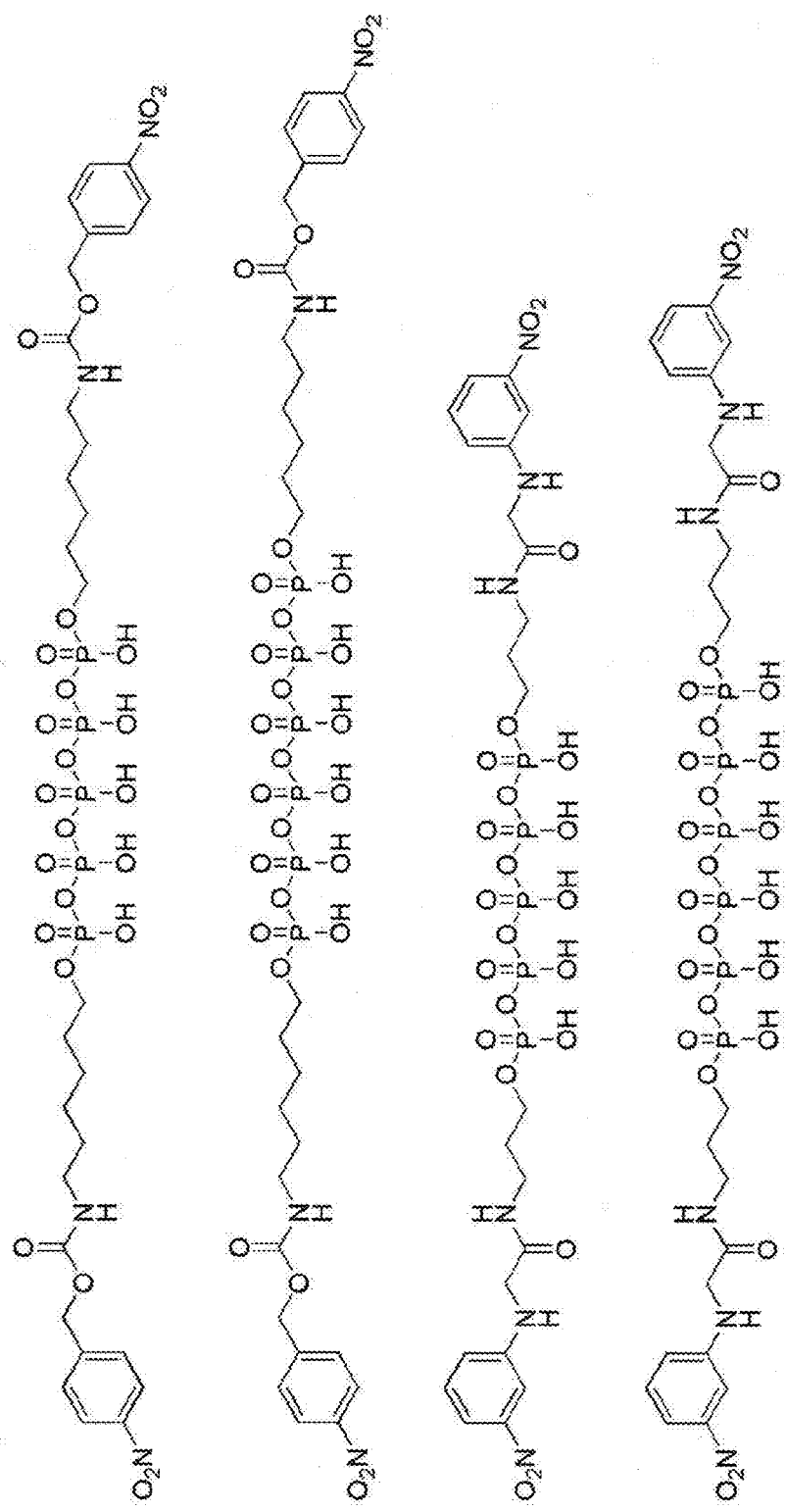
Figure 5A:
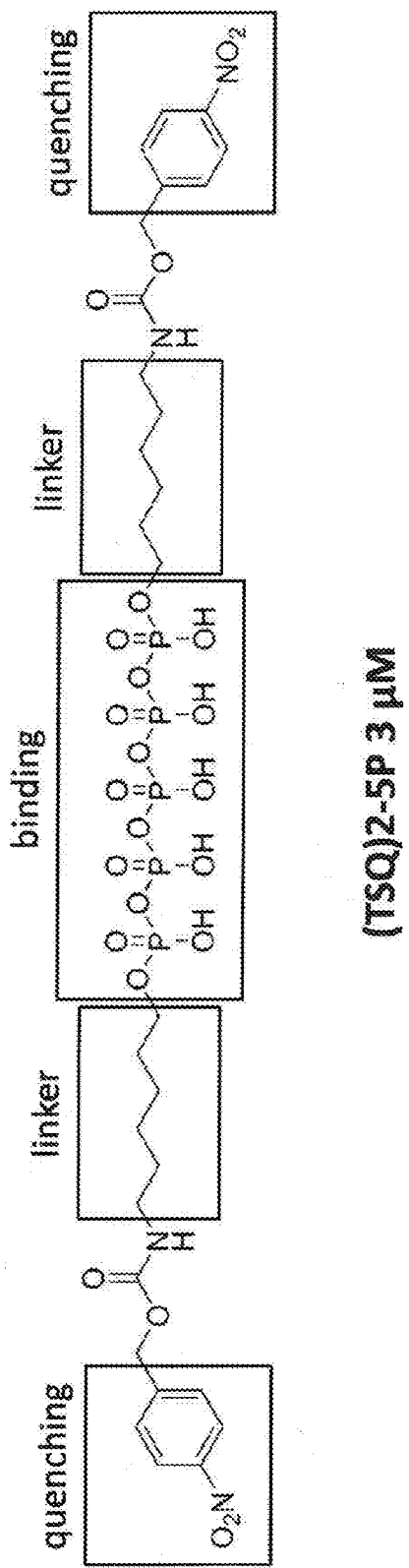
FIG. 5A is the formula of an exemplary compound of the invention ((TSQ)2-5P).
Figure 5B:
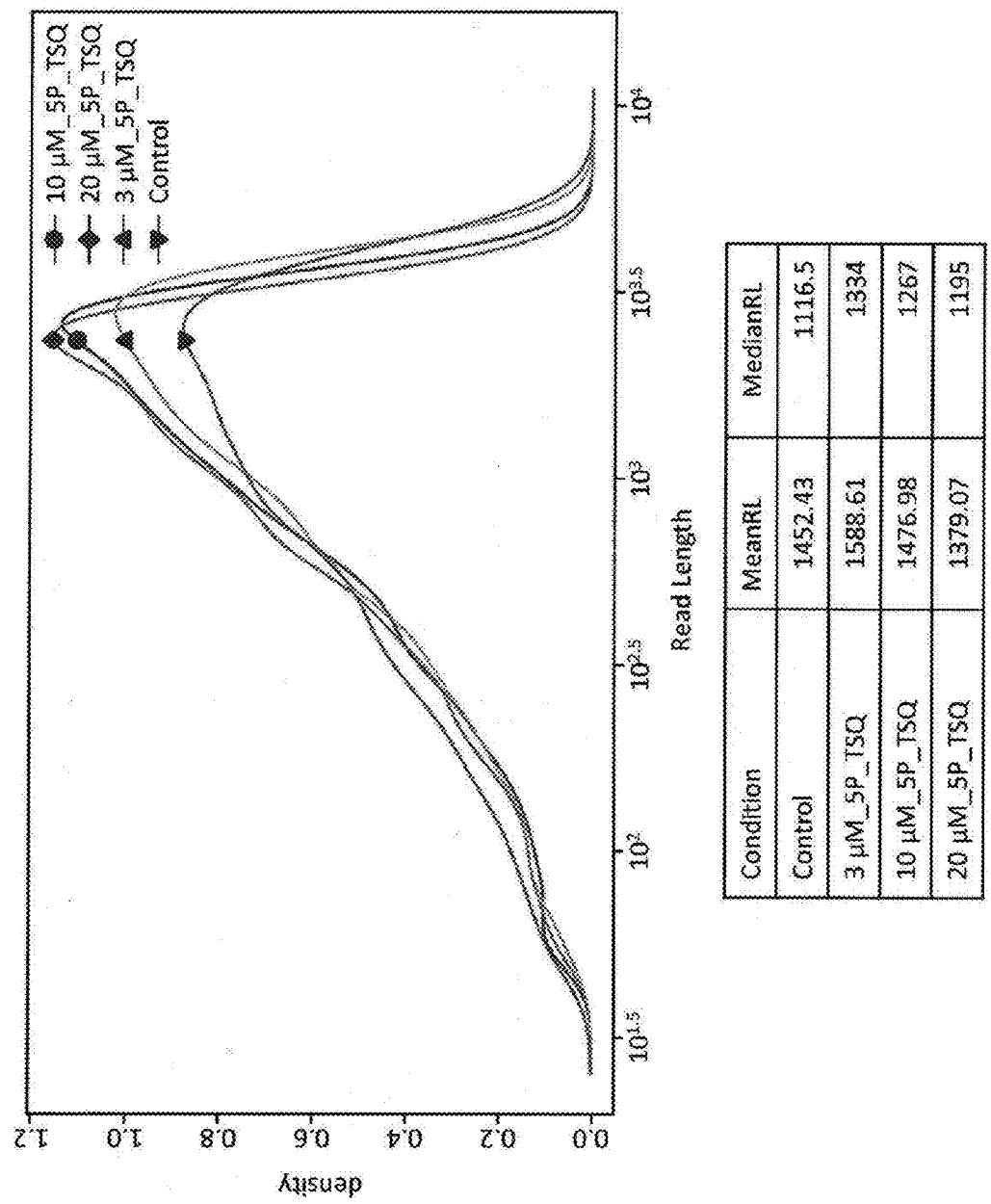
FIG. 5B is a graph showing the effect of (TSQ)2-5P on read length (RL) in a single molecule nucleic acid analysis.
Figure 5D:
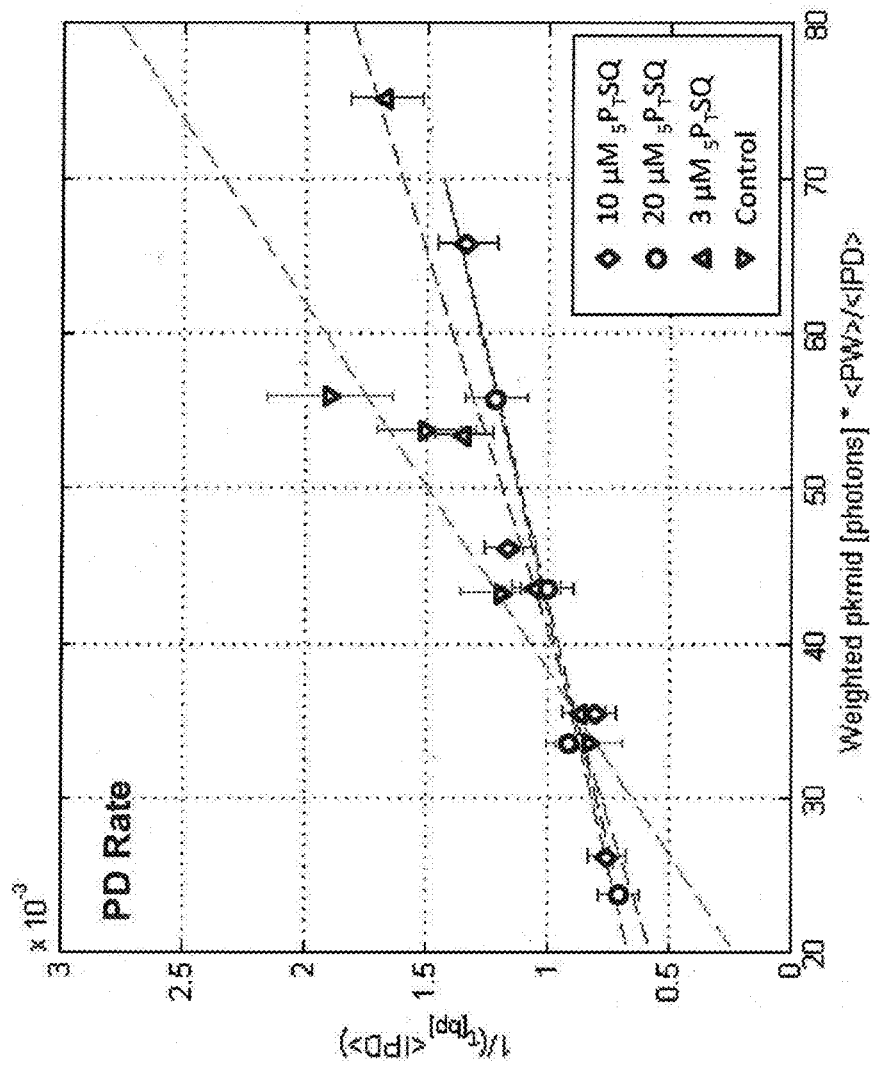
FIG. 5D is a graph showing the effect of (TSQ)2-5P on interpulse duration (IPD) in a single molecule nucleic acid analysis.
Figure 6:
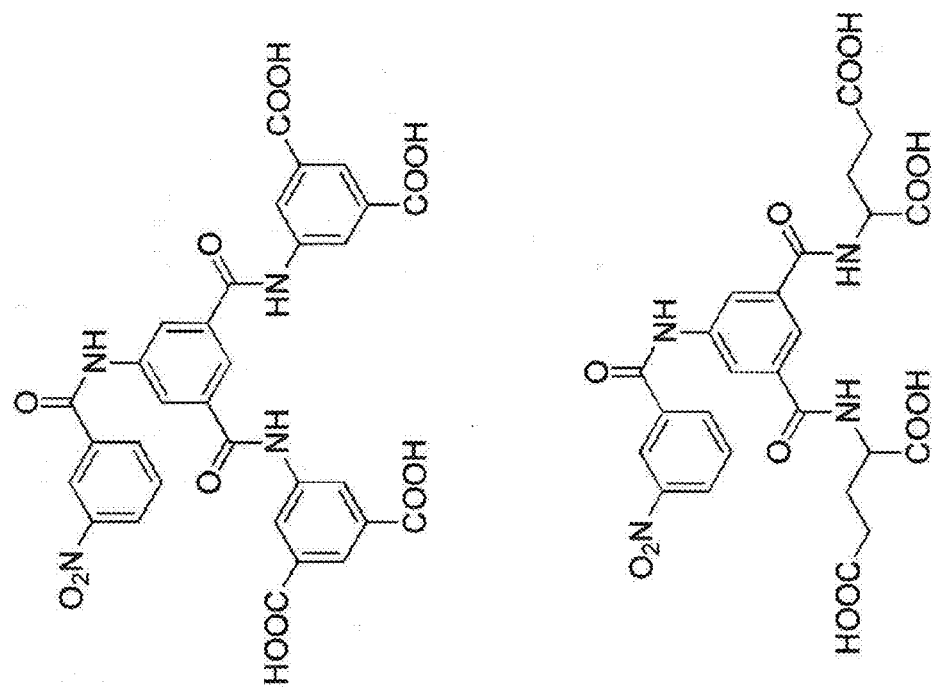
FIG. 6 provides the formulae of two exemplary polycarboxylic acid compounds of the invention.

The invention is further illustrated by the figures appended hereto. For example, FIG. 1A provides a formula of an exemplary compound of the invention according to a generic structural formula set forth in FIG. 1B. The compounds of FIG. 1 are mono-substituted with an exemplary photoprotective moiety, a triplet-state quencher moiety. The invention also provides compounds that are bis-substituted with a photoprotective moiety, e.g., a triplet-state quencher, such as those shown in FIGS. 3 and 4.

Synthesis

Figure 2A:
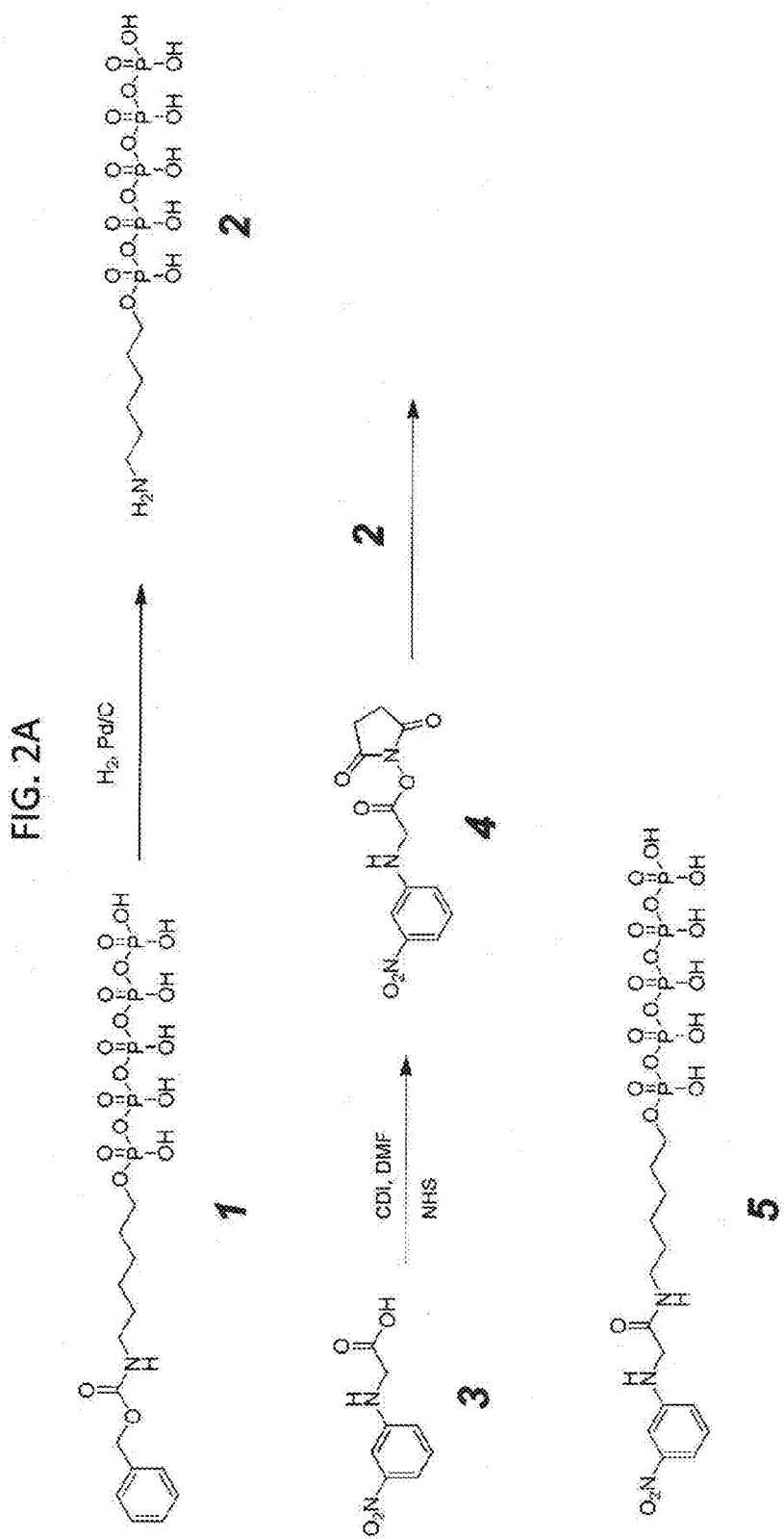
FIG. 2A-2B provides an exemplary synthetic route to compounds of the invention.
Figure 2B:
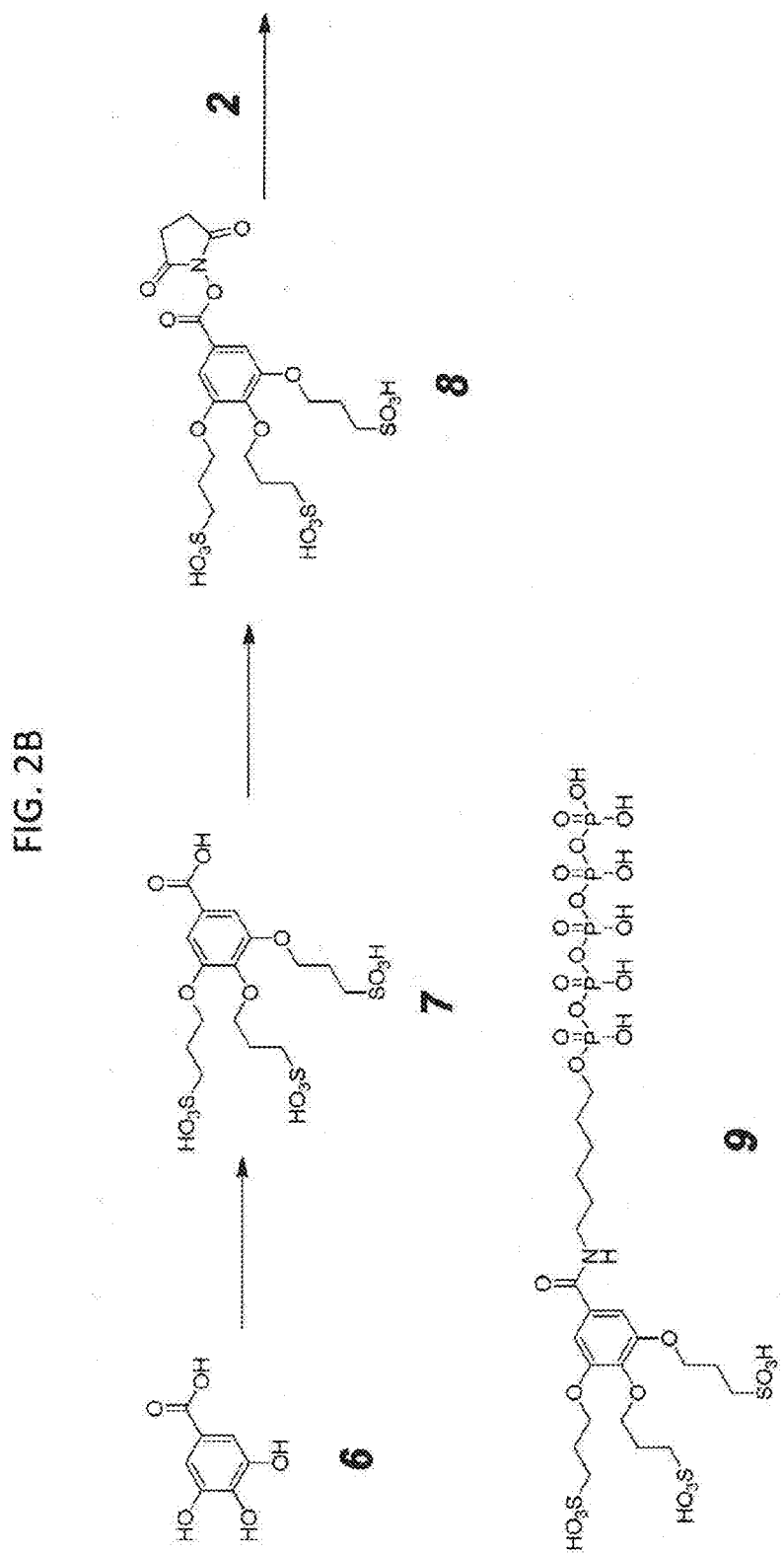

The compounds of the invention are readily synthesized from available precursors. An exemplary synthetic scheme is shown in FIG. 2. Thus, N-protected polyphosphate-(alkyl) compound 1 is deprotected under standard conditions providing free amine 2. Triplet-state quencher (TSQ) 3 is activated as the N-hydroxysuccinimide ester 4 and is reacted with amine 2 to form TSQ-(alkyl)-polyphosphate 5.

In various embodiments, a terminus or both termini of the polyphosphate moiety is/are conjugated with a species other than a triplet-state quencher, e.g., a charged moiety, a PEG-containing moiety, which is readily placed using chemistry similar to that set forth above. Thus, following a route similar to that outlined above, compound 9 is produced.

Reaction Mixtures

In various embodiments, the invention provides a reaction mixture including one or more photoprotective compound of the invention according to Formula I and/or Formula II as an additive. An exemplary reaction mixture of the invention includes a fluorescent or fluorogenic molecule, and an additive according to Formula I and/or Formula II. The reaction mixture optionally includes one or more additional reactants. In various embodiments, the one or more additional reactants includes one or more enzymes, reactive proteins, or ribozymes.

In an exemplary embodiment, the invention provides a reaction mixture including a first reactant, a second reactant comprising a fluorescent or fluorogenic label, and an additive according to Formula I and/or Formula H. The additive mitigates photo-induced damage to the first reactant in reaction mixtures in which interaction of the first and second reactants under excitation illumination results in photo-induced damage to the first reactant absent the additive.

In an exemplary embodiment, the reaction mixture includes one or more components of an assay, for example, an enzyme, reactive protein, or ribozyme. In various embodiments, the photoprotective agent reduces an amount of photo-induced damage to the enzyme, reactive protein, or ribozyme that would occur in the absence of the photoprotective agent. As will be appreciated by those of skill in the art, many enzymes, reactive proteins, or ribozymes are appropriate as components of assays, i.e., reaction mixtures. In exemplary embodiments of reaction mixtures of the invention, an enzyme component is selected from a polymerase, a ribosome, a nuclease, a helicase, a phosphatase, a protease, or a ligase enzyme; a reactive protein component is selected from an antibody and a lectin; and a ribozyme component is selected from 23S rRNA, RNaseP, CPEB3 ribozyme, and others known in the art (see, e.g., Doherty, et al. (2001) Annu Rev Biophys Biomol Struct 30: 457-475).

In various embodiments, the reaction mixture is a component of a nucleic acid assay (e.g., sequencing, SNP detection, PCR, etc.) and the reaction mixture further comprises a template nucleic acid molecule.

The reaction mixture can include one or more components for use in nucleic acid synthesis including, but not limited to, a nucleoside polyphosphate, or analog thereof, a primer, and a template nucleic acid molecule. In certain embodiments, the nucleoside polyphosphate has more than 3, 4, 5, or 6 phosphate groups. In certain embodiments, the nucleoside polyphosphate comprises a detectable label, e.g., a fluorescent dye. In various embodiments, the reaction mixture also includes an enzyme or enzyme complex capable of synthesizing a nucleic acid, e.g., a DNA polymerase, RNA polymerase, or reverse transcriptase.

The reaction mixture can include one or more components for use in protein synthesis including, but not limited to, a tRNA, an amino acid, and an mRNA template. In certain embodiments, the tRNA or amino acid comprises a detectable label, e.g., a fluorescent dye, e.g., as described in U.S. 2010/0317116, incorporated herein by reference in its entirety for all purposes. In various embodiments, the reaction mixture also includes an enzyme or enzyme complex capable of synthesizing a protein, e.g., a ribosome.

The compositions and methods of the invention are of use in reaction mixtures comprising substantially any fluorophore or fluorogenic molecule, for example, attached to a reaction component, e.g., a substrate for an enzyme. An exemplary fluorophore is a cyanine dye. In various embodiments, the fluorescent or fluorogenic molecule is a moiety conjugated to another assay component, e.g., nucleoside polyphosphate, tRNA, amino acid, or an analog thereof. Certain preferred fluorescent molecules and labeling strategies are provided in U.S. Patent Publication Nos. 2009/0208957, 2010/0255488, 2012/0058482, 201210058469, 2012/0052506, 2012/0077189, 2012/0058473; and in U.S. Ser. No. 61/649,058, filed May 18, 2012.

The compounds and reaction mixtures of the invention are of use to mitigate photo-induced damage in assays of a wide range of formats. In an exemplary embodiment, one or more components of the reaction mixture are contained within any useful vessel or instrument. In certain embodiments, the reaction mixture extends into a nanoscale aperture within a solid surface. In preferred embodiments, reaction sites at which the reaction is monitored have a very small observation volume, e.g., an effective observation volume that is less than one nanoliter ($10^{-9}$ liter), less than one picoliter, or less than one femtoliter, preferably on the order of zeptoliters. For example, the effective observation volume can be less than 1000 zeptoliters, 100 zeptoliters, 80 zeptoliters, or less than 50 zeptoliters, or even less than 10 zeptoliters. In an exemplary embodiment, at least one component of the reaction mixture is confined within a zero-mode waveguide. In certain preferred embodiments, the reaction mixture is applied to an array of nanoscale apertures, e.g., zero-mode waveguides. See, e.g., U.S. Pat. No. 7,476,503 for additional details on such arrayed substrates and their use in the performance of analytical reactions.

The additive according to Formula I or Formula II is included in the reaction mixture in any useful amount, which is readily determinable by those of skill in the art, e.g., using standard titration assays. In an exemplary embodiment, the additive is present at a concentration from about 0.5 µM to about 10 µM. In a further exemplary embodiment, the additive is present at a concentration from about 1 µM to about 5 µM. In various embodiments, the additive is present in a concentration of about 3 µM. These concentrations are far higher than the concentrations required for the photoprotective moieties absent the rest of the compound (e.g., not linked to a charged moiety such as a polyphosphate, polycarboxylate, polyphosphonate, polysulfonate, and the like, as described elsewhere herein), which typically are about 1 mM. In various embodiments, a first molar concentration (e.g., 3-5 µM) of the photoprotective compound according to Formula I or Formula II is as effective at mitigating photo-induced damage in a reaction mixture than a significantly higher molar concentration (e.g., 1 mM) of the photoprotective moiety (e.g., R or R') alone. For example, the molar concentration of the photoprotective compound according to Formula I or II that provides a given level of photoprotective benefit is typically 100- to 300-fold lower that the molar concentration of the photoprotective moiety alone required for the same level of photoprotective benefit. As such, use of these compounds allows the practitioner to use much less of the compound, e.g., 10-, 20-, 30-, 50-, 100-, 150-, 200-, or 300-fold less based on molar concentrations, than would be required using the photoprotective moiety (e.g., R or R') alone. Put another way, the compounds of the invention thus provide effective mitigation of photo-induced damage at a much lower concentration than the photoprotective moieties apart from the rest of the compound at the same molar concentration.

Figure 7:
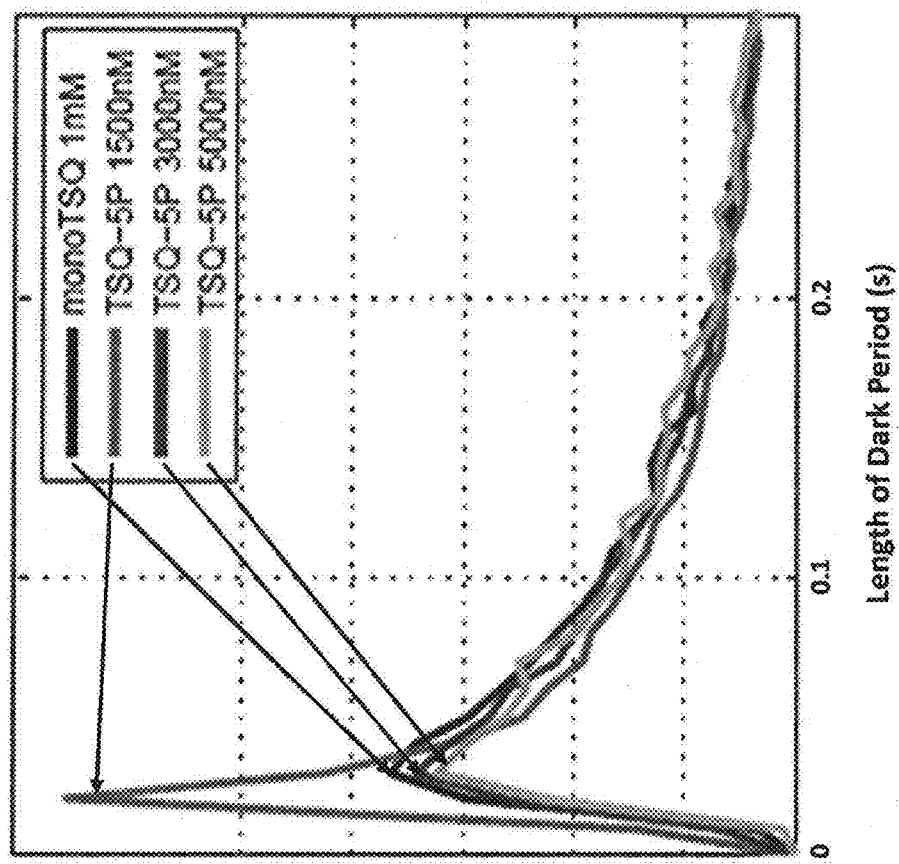
FIG. 7 provides exemplary data showing that 3 µM and 5 µM of the photoprotective compound referred to as "TSQ00'-6C-5P" in the Examples section is as effective at reducing the incidence of very short dark periods (proxy for blinkiness) as is 1 mM of a charged nitrophenyl photoprotective moiety

One measure of photoprotective benefit is monitoring "blinkiness" of dyes in a reaction mixture. For example, in a reaction in which dye-labeled reactants are being observed as they cyclically interact with an unlabeled reactant, the time between interaction events is a length of time during which no dye is present, or a "dark" period. Given certain reaction parameters, e.g., diffusion rates and concentration of the labeled reactant, a distribution of dark periods is measured that centers around a value that is an average time between interaction events. This distribution curve can be perturbed by dye blinking since such blinking introduces a very brief dark period during an interaction event. These blinking-induced dark periods introduce an aberrant peak in the dark period distribution resulting in a peak that is outside of the normal distribution and representing dark periods that are too short to be explained by the reaction parameters. Blinkiness is increased when a dye is excited to the triplet state and there is insufficient photo-induced damage mitigation to quickly return it to a non-triplet state. As such, addition of photoprotective compounds that prevent the triplet state or reduce the duration of the triplet state to a reaction mixture exhibiting this behavior can reduce or prevent this aberrant "short dark period" peak. This assay is useful for testing compounds for their ability to serve as photoprotective agents. FIG. 7 provides exemplary data showing that 3 µM and 5 µM of the photoprotective compound referred to as "TSQ001-6C-5P" in the Examples section is as effective at reducing the incidence of very short dark periods (proxy for blinkiness) as is 1 mM of the photoprotective moiety:

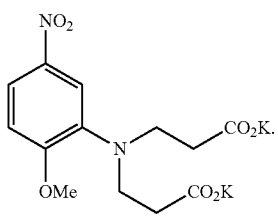

In various embodiments, the methods of the invention utilize more than one strategy for mitigating photo-induced damage. For example, a reaction mixture may include a compound according to Formula I or Formula II, as well as oxygen scavengers and/or reducing agents to prevent the formation of reactive oxygen. Alternatively, multiple compounds according to Formula I and/or Formula II can be included in a reaction mixture.

Devices

In an exemplary embodiment, the invention provides a device for use in performing an excitation illuminated reaction with a reaction mixture of the invention. An illustrative device includes a substrate having an observation region. In various embodiments a reaction component (e.g., an enzyme, ribozyme, antibody, or other reactive protein) is immobilized within the observation region, and a fluorescent or fluorogenic substrate or binding partner for the immobilized reaction component and a photoprotective agent of the invention are disposed within the observation region. Such an immobilized reaction component (e.g., enzyme, etc.) can be any component of use to perform the subject reaction. For example, exemplary enzymes include a polymerase, a ribosome, a helicase, a nuclease, or a ligase. Reactive proteins include proteins that bind substrates, such as antibodies and lectins. The device can also include the fluorescent or fluorogenic reactant, e.g., an enzyme substrate, ribozyme substrate, binding partner, reaction cofactor, etc.

An observation region of a device of the invention may include an area of a planar or other substrate surface upon which are immobilized reagents, e.g., enzymes. Alternatively, the observation region may include a physical confinement that constrains the reagents that are susceptible to photo-induced damage, including, e.g., microwells, nanowells, and/or planar surfaces that include hydrophobic barriers to confine reagents. As noted above, the present invention is particularly applicable to observation regions in which the damage susceptible reagents are present at concentrations or levels that photo-induced damage greatly impacts the reaction progress. This is particularly the case in immobilized reaction systems where additional, excess amounts of reagents cannot be provided in a bulk solution to obscure the impact of any damaged reagents.

In an exemplary embodiment, the observation region is, or is within, a zero-mode waveguide or another nanoscale aperture that provides a restricted and sub-nanoliter observation volume within which a reaction can be monitored.

Also provided is a kit for mitigating photo-induced damage while performing a reaction with a fluorescent or fluorogenic substrate for an enzyme in the presence of an enzyme. The kit includes the additive of Formula I and/or the additive of Formula II and directions for using the additive in an excitation illuminated reaction to mitigate photo-induced damage of one or more reactants. The kit optionally includes one or more reactant for the reaction, e.g., the enzyme.

Methods

In an exemplary embodiment, the invention provides a method for protecting an enzyme, ribozyme, or other reactive protein from photo-induced damage in an excitation illuminated reaction. An illustrative method includes querying the reaction mixture by illuminating it and detecting a signal emitted by a fluorophore or a fluorogenic molecule or moiety. In certain embodiments, the reaction mixture includes the enzyme, ribozyme, or other reactive protein; a photoprotective agent; and a fluorescent or fluorogenic molecule with which the enzyme, ribozyme, or other reactive protein will interact during the reaction. Upon illumination, the fluorescent or fluorogenic molecule (e.g., fluorescently labeled substrate for the enzyme, ribozyme, or reactive protein) produces a detectable signal. The photoprotective agent is preferably an additive according to Formula I and/or an additive according to Formula II. The photoprotective agent reduces an amount of photo-induced damage to the enzyme, ribozyme, or reactive protein resulting from interaction with the fluorescent or fluorogenic molecule under the excitation illumination to an amount that is less than that which would occur in the absence of the photoprotective agent. The photoprotective agent may also prevent or slow damage to other reaction components.

In various embodiments, the amount of photo-induced damage that occurs in a reaction mixture of the invention is detectably less than the amount of photo-induced damage that occurs in the absence of a photoprotective additive according to Formula I or Formula II. Photo-induced damage can be measured in different ways, depending on the particular analytical reaction. One way is by monitoring blinkiness of a fluorescent dye in the reaction, as further explained above. In other embodiments, the amount of photo-induced damage is measured as a length of time a reaction can proceed, e.g., the survival time for an enzyme catalyzing a reaction. For example, in a nucleic acid sequencing-by-synthesis reaction, a proxy for the level of photo-induced damage can be the length of the nascent strand synthesized and/or the length of the sequencing read generated. For example, the photoprotective agent increases an amount of time an enzyme, ribozyme, or reactive protein can perform a reaction before photo-induced damage terminates or otherwise perturbs its activity as compared to the reaction in the absence of the photoprotective agent. Typically, the photoprotective agent increases the average duration of the reaction as compared to the reaction in the absence of the photoprotective agent. The photoprotective agent can also increase the product formation and/or amount of data generated from the reaction to a level greater than that of the reaction in the absence of the photoprotective agent. Yet further the photoprotective agent can enhance the kinetic performance of the reaction, e.g., increasing the rate, fidelity, or processivity, such that the reaction performs detectably better based on one or more of these metrics than the reaction performed in the absence of the photoprotective agent.

Figure 8:
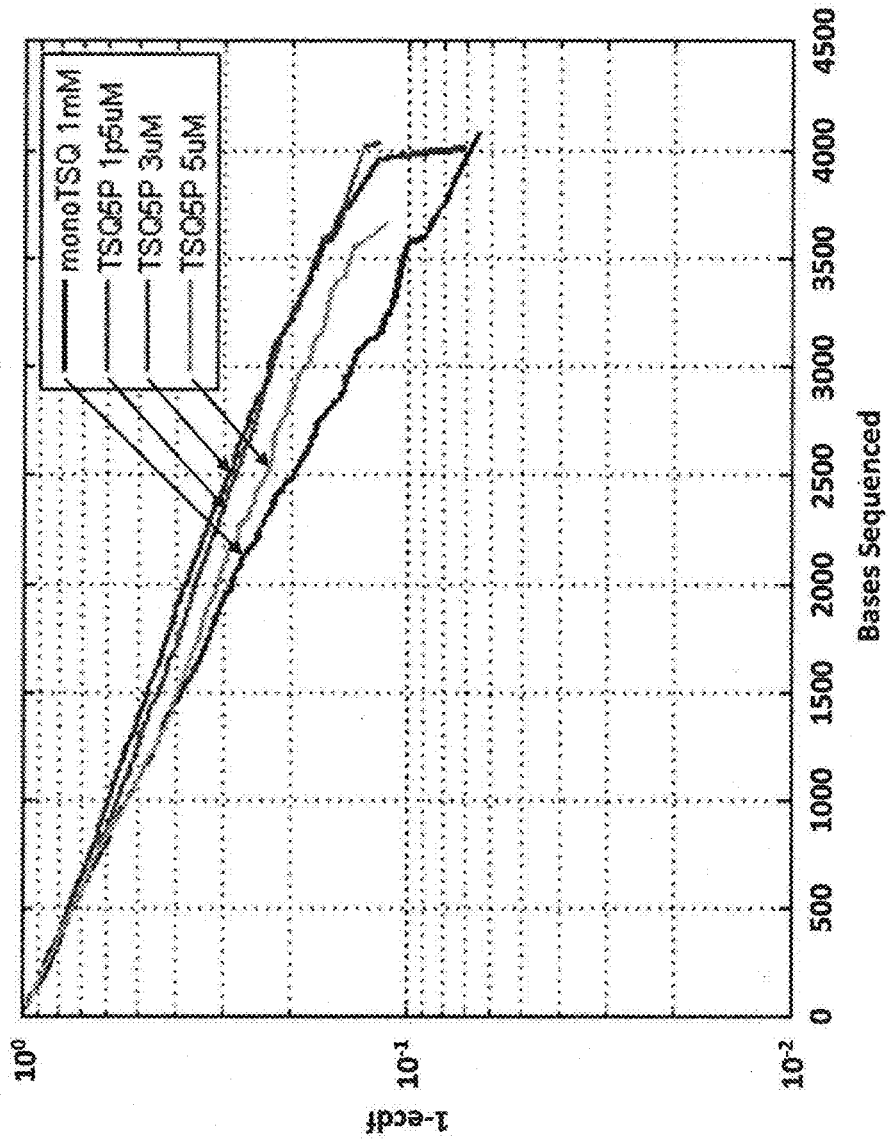
FIG. 8 illustrates results from an assay that monitored polymerase survival as a function of the number of bases sequenced during a sequencing-by-synthesis reaction. This data demonstrates that the photoprotective compound referred to as "TSQ00'-6C-5P" in the Examples section is more effective at increasing survival of a polymerase enzyme at 1.5, 3, and 5 µM than 1 mM of a charged nitrophenyl photoprotective moiety.

FIG. 8 illustrates results from an assay that monitored polymerase survival as a function of the number of bases sequenced during a sequencing-by-synthesis reaction. This data demonstrates that the photoprotective compound referred to as "TSQ001-6C-5P" in the Examples section is more effective at increasing survival of a polymerase enzyme at 1.5, 3, and 5 μM than 1 mM of the photoprotective moiety:

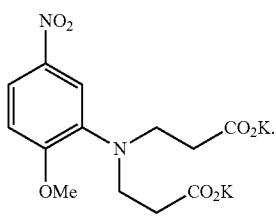

By various measures the polymerase survival in a sequencing-by-synthesis reaction is increased 15-25% in the presence of TSQ001-6C-5P as compared to the photoprotective moiety alone (data not shown).

A further example of an assay for measuring photo-induced damage comprises observing a polymerase enzyme as it performs nascent strand synthesis using a circular nucleic acid template, and counting the number of times the polymerase can pass around the template. In these examples, the laser power is typically increased to levels higher than those used in sequencing assays, since the object is to observe and measure photo-induced damage. The assay generally includes only two labeled nucleotides, where the incorporation (or multiple incorporations, e.g., opposite a block of complementary nucleotides) of one is indicative of a further pass around the template, and the other is being tested for its effect on photo-induced damage in the reaction, e.g. measured as a decrease in processivity of the enzyme. This allows the practitioner to separately analyze different dyes and photoprotective agents in a reaction in which photo-induced damage is expected to be enhanced. In such reactions, the photoprotective compounds of the invention are consistently as or more effective at mitigating photo-induced damage as are ~300-fold higher molar concentrations of the photoprotective moieties alone (e.g., not linked to a charged moiety such as a polyphosphate, polycarboxylate, polyphosphonate, polysulfonate, and the like, as described elsewhere herein). As such, the photoprotective agents of the present invention can be used to attain an equivalent or greater amount of protection as is attained using ~300-fold higher molar concentrations of the photoprotective moieties not linked to the charged moieties, and some experiments have even shown a 30-50% improvement in the processivity of the enzyme when using the photoprotective compounds of the invention as compared to the photoprotective moieties even at these drastically different concentrations.

The invention also provides methods of performing an illuminated reaction in a reaction mixture comprising an additive according to Formula I and/or Formula II. An exemplary method includes providing a substrate having a reaction mixture disposed thereon, wherein the reaction mixture comprises a first reactant, a second reactant and a photo-induced damage mitigating additive according to Formula I or Formula II, wherein the photo-induced damage mitigating agent reduces an amount of photo-induced damage to the first reactant resulting from interaction of the first reactant with the second reactant under excitation illumination that would occur in the absence of the additive. In preferred embodiments, the second reactant comprises a fluorescent or fluorogenic moiety. The reaction mixture is then illuminated on the substrate, with an excitation illumination. The reaction is preferably monitored in real time during the course of the reaction, e.g., by detection of emission radiation from the fluorescent or fluorogenic moiety.

In various embodiments, the invention provides methods of performing an analytical reaction within an observation region, preferably having a sub-nanoliter observation volume. In preferred embodiments, the analytical reaction comprises an enzyme, ribozyme, or other reactive protein. In preferred embodiments, the analytical reaction monitors the reaction volume within the observation region over time, e.g., in real time. Optionally, the analytical reaction is a single molecule reaction comprising a single molecule of a reaction component of interest (e.g., enzyme, ribozyme, or reactive protein) within the observation region. The single molecule is typically immobilized at a reaction site and contacted with fluorescent or fluorogenic reactants that interact with the single molecule (e.g., a substrate for an immobilized enzyme), and excitation radiation is directed at, and signals are detected from, the observation region. The mixture for the reaction also includes an additive according to Formula I and/or an additive according to Formula II. In an exemplary embodiment, the observation is for a period less than the photo-induced damage threshold period, which is lengthened in the presence of the additive according to Formula I. In an exemplary embodiment, photo-induced damage to the enzyme, the fluorophore (or fluorogenic substrate) or both is reduced relative to the amount of photo-induced damage in the absence of the additive of Formula I or Formula II.

Similarly, in various embodiments, the invention provides methods of monitoring a base extension reaction within an observation region. The method includes contacting the polymerase bound to a template nucleic acid with at least a first fluorescent or fluorogenic nucleotide analog, and monitoring a fluorescent signal emitted from the observation region in response to illumination with excitation radiation. The mixture also includes an additive according to Formula I and/or an additive according to Formula II. In an exemplary embodiment, the observation is for a period less than the photo-induced damage threshold period, which is lengthened in the presence of the additive according to Formula I and/or Formula II. In an exemplary embodiment, photo-induced damage to the polymerase, the fluorophore (or fluorogenic substrate) or both is reduced relative to the amount of photo-induced damage in the absence of the additive according to Formula I or Formula II. In related embodiments, a similar approach can be used to monitor other types of enzyme reactions, such as nuclease, helicase, topoisomerase, or kinase reactions, where inclusion of an additive according to Formula I and/or an additive according to Formula II reduces the amount of photo-induced damage to the enzyme, the fluorophore (or fluorogenic substrate), or both relative to the amount of photo-induced damage in the absence of the additive according to Formula I or Formula II. Further, the PID threshold is lengthened in the presence of the additive.

Similarly, in various embodiments, the invention provides methods of monitoring an antibody binding assay within an observation region. The method includes contacting the antibody with at least a first fluorescent or fluorogenic antigen, and monitoring a fluorescent signal emitted from the observation region in response to illumination with excitation radiation. The mixture also includes an additive according to Formula I and/or an additive according to Formula II. In an exemplary embodiment, the observation is for a period less than the photo-induced damage threshold period, which is lengthened in the presence of the additive according to Formula I and/or Formula II. In an exemplary embodiment, photo-induced damage to the antibody, the fluorophore (or fluorogenic substrate) or both is reduced relative to the amount of photo-induced damage in the absence of the additive according to Formula I or Formula II.

Yet further, in various embodiments, the invention provides methods of monitoring a protein synthesis reaction within an observation region. The method includes contacting a ribosome-mRNA complex with at least a first fluorescent or fluorogenic aa-tRNA (aminoacyl-tRNA), and monitoring a fluorescent signal emitted from the observation region in response to illumination with excitation radiation. The mixture also includes an additive according to Formula I and/or an additive according to Formula II. In an exemplary embodiment, the observation is for a period less than the photo-induced damage threshold period, which is lengthened in the presence of the additive according to Formula I and/or Formula II. In an exemplary embodiment, photo-induced damage to the ribosome, the fluorophore (or fluorogenic substrate), or both is reduced relative to the amount of photo-induced damage in the absence of the additive according to Formula I or Formula II.

With reference to nucleic acid analyses, it has been observed that, in template directed synthesis of nucleic acids using fluorescent nucleotide analogs as the substrate, prolonged illumination under such conditions yields substantial degradation in the ability of the polymerase to synthesize such DNA. Damage or even inactivation of polymerase enzymes diminishes the ability of the polymerase to continue processing a template nucleic acid during a synthesis reaction, which prevents the polymerase from completely processing long (e.g., greater than 1, 2, 3, 5, 10, or 15 kilobases in length) nucleic acid templates that the enzyme is able to process in the absence of the photo-induced damage. This reduction in processivity of the enzyme, in turn, leads to a reduction in read lengths for sequencing processes that identify sequence constituents based upon their incorporation into the nascent strand. As is appreciated in the art of genetic analysis, the length of contiguous reads of sequence directly impacts the ability to assemble genomic information from segments of genomic DNA.

Without being bound to a particular theory or mechanism of operation, it is believed that at least one cause of photo-induced damage to enzyme activity, particularly in the presence of fluorescence reagents, results from the direct interaction of the enzyme with photo-induced damaged fluorescent reagents. Further, it is believed that this photo-induced damage of the fluorescent reagents (and possibly additional damage to the enzyme) is at least partially mediated by reactive oxygen species that are generated during the relaxation of triplet-state fluorophores in the presence of molecular oxygen. In a proposed mechanism for this photo-induced damage, a fluorophore excited by exposure to electromagnetic radiation at an excitation wavelength transitions into a triplet state. Subsequent relaxation of the triplet-state fluorophore can then lead to generation of reactive oxygen species, which can damage one or both of the fluorophore or the enzyme processing the fluorophore, e.g., the polymerase, as well as other reaction components that may be proximal to the triplet-state fluorophore. Accordingly, in various embodiments, the present invention is directed to inclusion within the illuminated reaction mixture of one or more agents according to Formula I or Formula II that function to block or otherwise minimize the pathways that lead to such photo-induced damage, thus preventing downstream damage to enzymes within the system. As such, in various embodiments the photo-induced damage mitigating agent is a triplet-state quencher.

In various embodiments, the methods of the invention utilize more than one strategy for mitigating photo-induced damage. For example, a reaction mixture may comprise a combination of a compound according to Formula I, a compound of Formula II, and oxygen scavengers, and/or reducing agents to prevent or reduce photo-induced damage, e.g., caused by the formation of reactive oxygen.

While researchers have provided methods and compositions for limiting photo-induced damage to fluorophores (see, e.g., Altman et al., *Nature Methods*, 9, 68-71 (2012); Altman et al., *Nature Methods*, 9: 428-429 (2012)), the negative impacts of downstream photo-induced damage to enzymatic systems in the presence of and/or resulting from photodestruction of fluorescent reagents has not been conclusively resolved. For ease of discussion, the detrimental impact of the photo-induced damage event, whether resulting from actual damage to a given reagent or from interaction with a damaged reagent, is generally referred to herein as photo-induced damage.

Again, the definition of an agent as a photoprotective agent is generally reflective of the impact that such agent has on the actual photo-induced damage event or the downstream impacts of that damage. As such, a photoprotective agent may prevent photo-induced damage of one or more reagents, or it may mitigate the impact that a photo-induced damaged reagent may have on a particular, limited reagent in the reaction of interest. By way of example, an agent that blocks a detrimental interaction between a photo-induced damaged fluorescent compound and a critical enzyme component would still be referred to as a photoprotective agent, regardless of the fact that it did not prevent the initial photo-induced damage to the fluorescent or other reagent.

Measurements of reduction of photo-induced damage as a result of inclusion or treatment with a photo-induced damage mitigating agent may be characterized as providing a reduction in the level of photo-induced damage over an untreated reaction. Further, characterization of a reduction in photo-induced damage generally utilizes a comparison of reaction rates, e.g., enzyme activity, and/or a comparison of the photo-induced damage threshold period, between a treated reaction mixture and an untreated reaction mixture.

In the case of the present invention, the inclusion of photoprotective agent(s) according to Formula I or Formula II generally results in a reduction of photo-induced damage of one or more reactants in a given reaction. A reduction of photo-induced damage can be measured in terms of prevented loss of reactivity, e.g., enzyme activity, in the system, of at least 10%, preferably, greater than 20%, and more preferably, greater than about a 50% reduction, and in many cases greater than a 90% and up to and greater than 99% reduction in such photo-induced damage. By way of illustration, and purely for the purpose of example, when referring to reduction in photo-induced damage as a measure of enzyme activity in the presence and absence of the photo-induced damage mitigating agent, if a reaction included a reaction mixture having 100 units of enzyme activity that would, in the absence of a photo-induced damage mitigating agent, and following illuminated analysis, yield a reaction mixture having only 50 units of activity, then a 10% reduction in photo-induced damage would yield a final reaction mixture of 55 units (e.g., TO % of the 50 units otherwise lost, would no longer be lost).

A reduction of photo-induced damage can also be measured in terms of a lengthening of the duration of an analytical reaction. By way of illustration, and purely for the purpose of example, when referring to reduction in photo-induced damage as a measure of reaction duration in the presence and absence of the photo-induced damage mitigating agent, consider a reaction including a reaction mixture wherein an enzyme becomes inactivated after 50 minutes (on average) in the absence of illumination, but becomes inactivated after 10 minutes (on average) under illumination in the absence of a photo-induced damage mitigating agent. In this case, the enzyme suffers an 80% decrease in the length of time it is active under illumination conditions as compared to non-illuminated conditions. As such, 50% reduction in photo-induced damage would be expected to yield a final reaction duration of 30 minutes (e.g., 50% of the 40 minutes otherwise lost, would no longer be lost).

A reduction of photo-induced damage can also be measured in terms of an increase in product formation during an analytical reaction. By way of illustration, and purely for the purpose of example, when referring to reduction in photo-induced damage as a measure of product formation in the presence and absence of the photo-induced damage mitigating agent, consider a reaction including a reaction mixture wherein a polymerase can synthesize a nascent strand that is 10 kb in length in the absence of illumination, but only 1 kb in length under illumination in the absence of a photo-induced damage mitigating agent. In this case, the enzyme suffers a 90% decrease in the length of the nascent strand synthesized under illumination conditions as compared to non-illuminated conditions. As such, 67% reduction in photo-induced damage would be expected to facilitate production of a nascent strand that is about 6 kb in length (e.g., 67% of the 9 kb otherwise not synthesized, would be synthesized).

In accordance with the methods of the present invention, photoprotective agents may generally be provided as a component of the reaction mixture, either through addition as an additive, either liquid or solid, or through predisposition and/or immobilization of the photo-induced damage mitigating agents within the region where the reaction is taking place. By way of example, in cases where the reaction of interest is confined to a particular region or location, it may be desirable to immobilize or otherwise localize the photoprotective agents within or proximal to that region. Likewise, where a reaction mixture comprises cooperatively functioning components, e.g., dual enzyme systems, it may again be desirable to localize such components relative to each other, as well as to the reaction of interest.

The present invention also provides methods of mitigating the impact of photo-induced damage on the results of a given analytical operation by only interrogating a reaction mixture, e.g., detecting fluorescent emission, during such portion of the illumination period before which excessive photo-induced damage has occurred (e.g., based upon the PID threshold of the reaction), and by enhancing the length of time a reaction mixture is irradiated before a component is excessively damaged by including an additive according to Formula I or Formula II within the reaction mixture. This approach is particularly useful in the optical interrogation of reactions where components of the reaction that are susceptible to photo-induced damage are spatially confined on an assay substrate, e.g., within a sub-nanoliter observation volume such as within a zero-mode waveguide, either through the presence of structural confinements and/or through immobilization of the components. Examples of such confined reagents include surface immobilized or localized reagents, e.g., surface immobilized or associated enzymes, antibodies, etc. that are interrogated upon the surface, e.g., through fluorescence scanning microscopy or scanning confocal microscopy, total internal reflectance microscopy or fluorometry, surface imaging, or the like.

As noted above, the methods and compositions of the invention are useful in a broad range of optically detected analytical reactions, and particularly those using photoluminescent or fluorescent reactants, and particularly such reactions where the reagents that are susceptible to photo-induced damage are present at relatively low levels. One exemplary application of the methods and compositions described herein is in single molecule analytical reactions, where the reaction of a single, or very limited number of molecules are observed in the analysis, such as observation of the action of a single enzyme molecule. In particular, when an analysis is relying upon a small population of reagent molecules, damage to any significant fraction of that population will have a substantial impact on the analysis being performed.

One example of a single molecule analysis includes sequencing of nucleic acids by observing incorporation of nucleotides into a nascent nucleic acid sequence during template directed polymerase based synthesis. Such methods, generally referred to as "sequencing by incorporation," involve the observation of the addition of nucleotides or nucleotide analogs in a template dependent fashion in order to determine the sequence of the template strand. A number of processes for performing this detection include the use of fluorescently labeled nucleotide analogs within a confined observation region, e.g., within a nanoscale well or tethered, either directly or indirectly to a surface. By illuminating and detecting the fluorescent bases that are incorporated, or are to be incorporated into the nascent strand, one can ascertain the nature of the base, and as a result, the complementary base in the template strand.

One particularly preferred aspect of the invention is in conjunction with the sequencing by incorporation of nucleic acids within an optical confinement, such as a zero-mode waveguide, in which one is observing an extremely small reaction volume in which one or only a few polymerase enzymes and their fluorescent substrates may be present. Zero-mode waveguides, and their use in sequencing applications is generally described in U.S. Pat. Nos. 6,917,726, 7,315,019, and 7,056,661, and preferred methods of sequencing by incorporation are generally described in Published U.S. Patent Application No. 2003-0044781, the full disclosures of which are incorporated herein by reference in their entirety for all purposes.

As will be appreciated, prolonged interrogation of a limited population of reagents, e.g., fluorescent analogs and confined polymerase enzymes can lead to photo-induced damage of the various reagents to the point of substantially impacting the activity or functionality of the polymerase enzyme. In particular, it has been shown that prolonged illumination of DNA polymerases involved in synthesis using fluorescent nucleotide analogs results in a dramatic decrease in the enzyme's ability to synthesize DNA. Without being bound to any theory of operation, it is believed that the photo-induced damage event affects the catalytic region of the enzyme thus affecting either the ability of the enzyme to remain complexed with the template, or its ability to process additional synthesis.

In accordance with the present invention, the above-described sequencing reaction may be carried out in the presence of one or more photo-induced damage mitigating agents, as described above.

In general, the photo-induced damage mitigating agents are present in the reaction mixture at levels sufficient to provide beneficial impact, e.g., reduced photo-induced damage and/or extension of the photo-induced damage threshold period, but are not present at such levels as to interfere with the reaction of interest, e.g., the sequencing reaction. Concentrations of the components of a photo-induced damage mitigating agent will generally vary by application. By way of example, an additive according to Formula I or Formula II is present, in some embodiments, from about 0.5 µM to about 10 µM. In some embodiments, the additive is present at a concentration from about 1 µM to about 5 µM. In various embodiments, the additive is present in a concentration of about 3 µM. For immobilized assay systems, the amount of immobilized reagents will generally provide activity levels that correspond to the activity levels of the aforementioned concentrations in non-immobilized formats. Precise amounts of reagents will generally depend upon the relative efficiency of the immobilization process, and resulting activity of the immobilized components.

The following non-limiting examples are provided to further illustrate the invention.

EXAMPLES

The following non-limiting examples illustrate methods of making and using various photoprotective compounds of the invention. Because of the value of single molecule analysis in nucleic acid sequencing applications, DNA polymerase systems were used to identify the impact of photo-induced damage and its solutions in accordance with the present invention. Assays were run to identify the scope and/or nature of photo-induced damage to polymerase reactions.

Example 1

Sequencing-by-Synthesis Assays to Measure Photo-Induced Damage

Experiments were conducted using a single-molecule, real-time (SMRT®) sequencing instrument. (For detailed information on experiments, see, e.g., Eid, et al. (2009) Science 323:133-138; and U.S. Patent Publication No. 2012/0052488, both of which are incorporated herein by reference in their entireties for all purposes.) Briefly, 30 nM of a phi29 polymerase enzyme modified for immobilization was mixed with 10 nM of a circular DNA template/primer complexes and other reaction mixture components, including nucleotide analogs bearing a phospholinked fluorescent dye in MOPS buffer, pH 7.5. The mixture was incubated at 37° C. to allow formation of polymerase/template/primer complexes. The mixture was then diluted and an aliquot was added to a zero-mode waveguide array, which was incubated to allow immobilization of the complexes within zero-mode waveguides on the array. After washing, a solution comprising fluorescently labeled nucleotides and photoprotective agents was added and the array was placed inside the sequencing instrument. Sequencing was initiated and reactions were monitored in real time. The fluorescence emissions were recorded, processed, and analyzed.

Analysis of the fluorescent emissions included measurement of the time between pulses, also known as "interpulse duration" or IPD. Detection of a peak of very small IPDs, e.g., less than 0.1 seconds in length, is indicative of fluorophore blinking, which is a proxy for insufficient mitigation of photo-induced damage in the reaction. Compounds were compared in their ability to reduce this peak as a measure of their effectiveness as photoprotective agents at various concentrations.

Further analysis of the fluorescent emissions included measurement of polymerase enzyme survival in the reaction as a function of number of bases sequenced. Another measure of photo-induced damage was the average read length produced in the sequencing reaction.

The propensity for photo-induced damage in the presence of different dyes and different photoprotective agents was also tested using a reaction system that used laser powers higher than the laser power typically used in sequencing reactions as a means to increase the photo-induced damage and, therefore, the opportunity to measure it. These assays used a small, circular template having a short homopolymer region that served a clocking function to count the number of times a polymerase processed the template. The polymerase reactions were performed using two dye-labeled nucleotides and two unlabeled nucleotides. One of the dye-labeled nucleotides comprised a dye known to have low photo-induced damage under the reaction conditions being used, and these nucleotides were complementary to the homopolymer region. As such, each time a set of pulses was detected that corresponded to these labeled nucleotides, it was known that the polymerase had gone around the circular template again. The second dye-labeled nucleotide comprised a dye to be tested for its ability to cause photo-induced damage in the reaction ("test dye"). The test dye and excitation illumination (e.g., wavelength, intensity, etc.) could be varied between reactions, and the base in the nucleotide linked to the test dye was also varied to change the sequence context within which the nucleotide linked to the test dye was incorporated. In these reactions, since the nucleotides are linked to the dyes on a terminal phosphate, incorporation of the constituent nucleotide monophosphate by the polymerase causes release of the dye. That is, the nascent strand is a native polynucleotide and does not comprise the dye label.

Example 2

Synthesis of Various Embodiments of Additives of Formula I

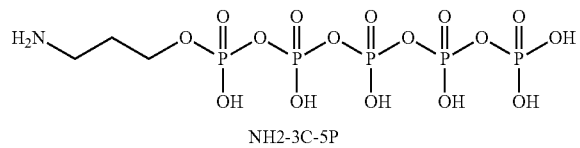 [SMILES: NCCCOP(=O)(O)OP(=O)(O)OP(=O)(O)OP(=O)(O)OP(=O)(O)O]

NH2-3C-5P

To a solution of N-FMoc-aminopropanol (124 mg, 417 µmol) and triethylamine (64 µL, 417 mmol) in dichloromethane (2 mL) in an ice bath was added phosphorus oxychloride ($POCl_3$, 39 µL, 417 µmol) under nitrogen atmosphere. After stirring 10 min at 0° C. a solution of tributylammonium pyrophosphate (1.14 g, 2.085 mmol) and triethylamine (571 µL, 4.2 mmol) in DMF (2 mL) was added dropwise and stirred overnight at ambient temperature. To the solution was added a TEAB buffer (1M, 10 mL) and stirred overnight at ambient temperature. The filtrate was concentrated under reduced pressure to small volume, which was then subjected to HPLC purification to give the desired product together with small amount of the diphosphate, triphosphate, tetraphosphate, hexaphosphate and polyphosphate. To the pentaphosphate product was then added $NH_4OH$ (1 mL) and reacted overnight. Concentrated to dryness, washed with EtOAc (3×5 mL), decanted the solvent and dried to give (37.4 mg, 12% yield) of the desired product. Other by-products, such as NH2-3C-5P-3C—NH2 was also isolated and used in later reaction.

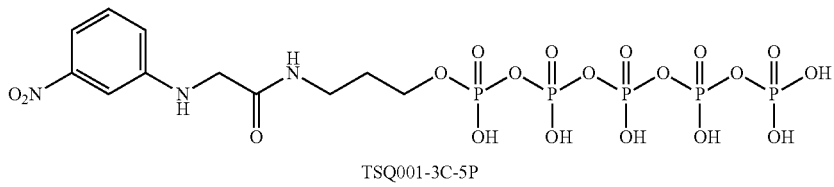 [SMILES: O=C(CNc1cccc([N+](=O)[O-])c1)NCCCOP(=O)(O)OP(=O)(O)OP(=O)(O)OP(=O)(O)OP(=O)(O)O]

TSQ001-3C-5P

To a solution of TSQ001 (1.5 mg, 5.4 μmol) in DMF (100 μL) was added excess of carbonyldiimidazole (CDT, 7.0 mg, 43 μmol) and N-hydroxysuccinimide (NHS, 1.5 mg, 14 μmol) and stirred for 16 h at ambient temperature. To it was added 0.2 M sodium bicarbonate pH 8.3 buffer (10 μL) followed by a solution of NH2-3C-5P (4 μmol) in 0.2 M sodium bicarbonate pH 8.3 buffer (100 μL). The resultant solution was stirred overnight and then subjected to reverse-phase HPLC (acetonitrile/0.1 M TEAB gradient) purification to give 0.56 μmol of a product (14% yield) after evaporation of solvent.

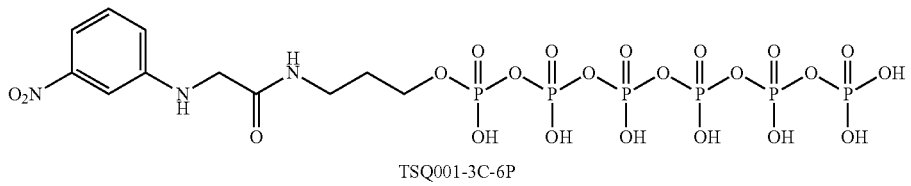 [SMILES: O=C(CNc1cccc([N+](=O)[O-])c1)NCCCOP(=O)(O)OP(=O)(O)OP(=O)(O)OP(=O)(O)OP(=O)(O)OP(=O)(O)O]

TSQ001-3C-6P

To a solution of TSQ001 (1.7 mg, 5.7 μmol) in DMF (100 μL) was added excess of carbonyldiimidazole (CDT, 7.0 mg, 43 μmol) and N-hydroxysuccinimide (NHS, 1.5 mg, 14 μmol) and stirred for 16 h at ambient temperature. To it was added 0.2 M sodium bicarbonate pH 8.3 buffer (10 μL) followed by a solution of NH2-3C-6P (4 μmol) in 0.2 M sodium bicarbonate pH 8.3 buffer (100 μL). The resultant solution was stirred overnight and then subjected to reverse-phase HPLC (acetonitrile/0.1 M TEAB gradient) purification to give 0.46 μmol) of a product (12% yield) after evaporation of solvent.

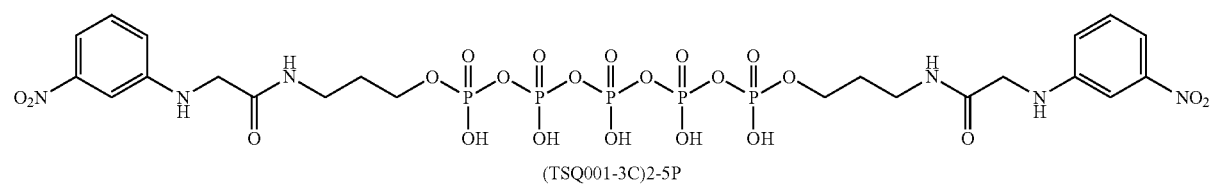 [SMILES: O=C(CNc1cccc([N+](=O)[O-])c1)NCCCOP(=O)(O)OP(=O)(O)OP(=O)(O)OP(=O)(O)OP(=O)(O)OCCCNC(=O)CNc1cccc([N+](=O)[O-])c1]

(TSQ001-3C)2-5P

To a solution of TSQ001 (3.80 mg, 12.8 μmol) in DMF (50 μL) was added excess of carbonyldiimidazole (CDI, 7.0 mg, 43 μmol) and N-hydroxysuccinimide (NHS, 1.5 mg, 14 μmol) and stirred for 16 h at ambient temperature. To it was added 0.2 M sodium bicarbonate pH 8.3 buffer (10 μl) followed by a solution of NH2-3C-5P-3C—NH2 (5.06 μmol) in 0.2 M sodium bicarbonate pH 8.3 buffer (50 μl). The resultant solution was stirred overnight and then subjected to reverse-phase HPLC (acetonitrile/0.1 M TEAB gradient) purification to give 0.66 μmol) of a product (13% yield) after evaporation of solvent.

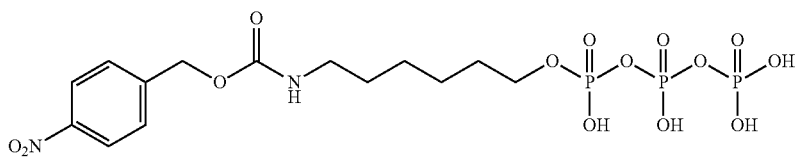

PNZ-6C-3P

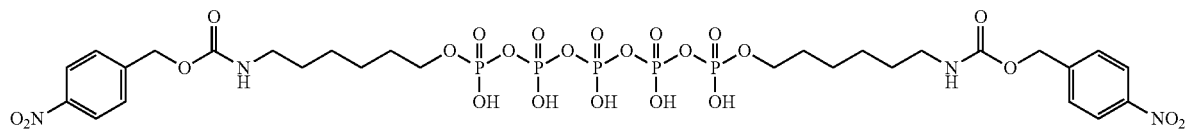

(PNZ-6C)2-5P

To a solution of PNZ-6C (317.3 mg, 1.07 mmol, prepared from para-nitrobenzyl chloride and 6-amino-1-hexanol) in dichloromethane (5.0 mL) in an ice bath was added triethylamine (167 µl, 1.2 mmol) and phosphorus oxychloride (POCl$_3$, 100 µl, 1.07 mmol) under nitrogen atmosphere. After stirring 10 min at 0° C. a solution of tributylammonium pyrophosphate (587 mg, 1.07 mmol) and triethylamine (334 µl, 2.4 mmol) in DMF (10 mL) was added dropwise and stirred for 3 h at ambient temperature. To the solution was added a TEAB buffer (1M, 10 mL) and stirred overnight at ambient temperature. The filtrate was concentrated under reduced pressure to small volume, which was then subjected to ion-exchange and reverse-phase HPLC purification to give the desired product (36.05 mg, (10% yield) together with small amount of the diphosphate, tetraphosphate, pentaphosphate and hexaphosphate and polyphosphate. Other bis-product were also isolated and identified by LC/MS and assigned to (PNZ-6C)2-2P, (PNZ-6C)2-3P, (PNZ-6C)2-4P, (PNZ-6C)2-5P (see above), (PNZ-6C)2-6P.

uct was synthesized as the major product using the following procedure. To a solution of PNZ-6C (1.20 g, 4.05 mmol, prepared from para-nitrobenzyl chloride and 6-amino-1-hexanol) in dichloromethane (20 mL) in an ice bath was added tributylamine (4.824 mL, 20.2 mmol) and phosphorus oxychloride (POCl3, 377 µl, 4.05 mmol) under nitrogen atmosphere. After stirring 1 h at ambient temperature a solution of tributylammonium pyrophosphate in acetonitrile (18 mL, 0.225 M, 4.05 mmol) was added and stirred for 1 h. A solution of additional of tributylammonium pyrophosphate in DMF (12.15 mmol, 54 mL) was added followed by addition of magnesium chloride (2.699 g, 28.3 mmol) and stirred overnight. To the solution was added a TEAB buffer (1M, 100 mL) and then EDTA solution (0.5 M, 100 mL). The mixture was then filtered through Celite to remove the solid particle. The filtrate was concentrated under reduced pressure to small volume, which was then subjected to HPLC purification to give a mixture of mainly the desired

PNZ-6C-4P

The product was obtained as a by-product from the synthesis of the PNZ-6C-3P above.

product together with tetraphosphate and triphosphate by-products. The mixture solution was then subjected to ion-

PNZ-6C-5P

The product was obtained as a by-product from the synthesis of the PNZ-6C-3P above. Alternatively, the prodexchange purification to give the desired product, 1.77 g (yield ~40%) as a triethylamine salt.

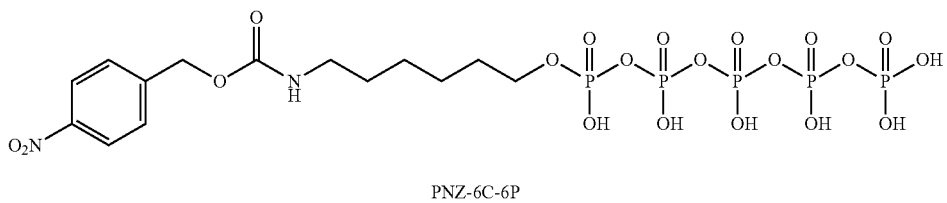 [SMILES: O=C(NCCCCCCOP(=O)(O)OP(=O)(O)OP(=O)(O)OP(=O)(O)OP(=O)(O)O)OCc1ccc([N+](=O)[O-])cc1]

PNZ-6C-6P

The product was obtained as a by-product from the synthesis of the PNZ-6C-3P above.

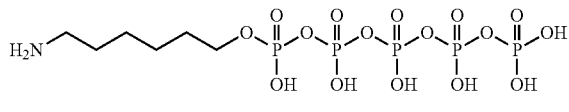

NH2-6C-5P

To a solution of PNZ-6C-5P (1.182 g, 1.28 mmol) in methanol (20 mL) was added palladium on activated charcoal (10% Pd, 2.05 g), 1,4-cyclohexadiene (8.00 mL, 84.6 mmol) and triethyl amine (328 µl) at room temperature in a 30 mL vial with closed cap. The mixture was stirred at 50° C. for 7 h and then ambient temperature overnight. Filtered the mixture through a pad of Celite and washed with methanol (2×30 mL). The solvent was evaporated to dryness and the residue was dissolved in 0.1 M TEAB (20 mL) and washed with ethyl acetate (20 mL×3). The aqueous layer was evaporated to dryness, coevaporated three times with methanol to give an oil (0.846 g) of product as triethylammonium salt. The product was then dissolved in methanol, to it was added DIPEA (958 mg) and co-evaporated four times with methanol to dryness. The residual product (as an DIPEA salt) was then dissolved in water (5.075 mL) to give a stock solution of the product (180.76 mM).

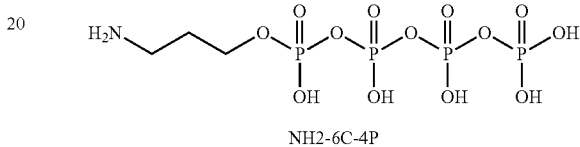

NH2-6C-4P

To a solution of PNZ-6C-4P (30 µmol) in water (350 µl) was added 10% Pd/C (40 mg) and equipped with a hydrogen balloon. After stirring overnight at ambient temperature the solution was diluted with water and passed through a pad of celite. The filtrate was concentrated and re-dissolved 0.2 M sodium bicarbonate pH 8.3 buffer (100 µl) to give a stock solution of NH2-6C-4P (30 µmol/100 µl).

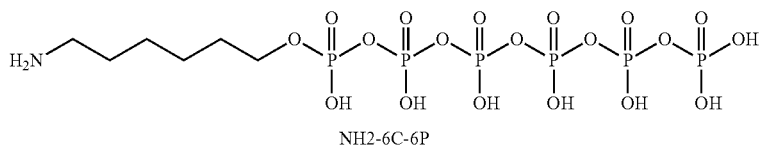 [SMILES: NCCCCCCOP(=O)(O)OP(=O)(O)OP(=O)(O)OP(=O)(O)OP(=O)(O)OP(=O)(O)O]

NH2-6C-6P

To a solution of PNZ-6C-6P (11.7 µmol) in water (1.0 mL) was added 10% Pd/C (16 mg) and equipped with a hydrogen balloon. After stirring overnight at ambient temperature the solution was diluted with water and passed through a pad of celite. The filtrate was concentrated and re-dissolved 0.2 M sodium bicarbonate pH 8.3 buffer (100 µl) to give a stock solution of NH2-6C-6P (11.7 µmol/100 µl).

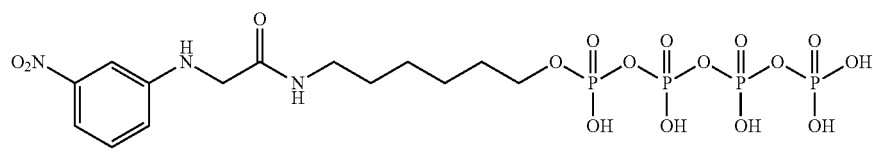

TSQ001-6C-4P

TSQ001 (1.6 mg, 5.4 µmol) in DMF (50 µl) was added excess of carbonyldiimidazole (CDI, 7.0 mg, 43 µmol) and N-hydroxysuccinimide (NHS, 1.5 mg, 14 µmol) and stirred for 16 h at ambient temperature. To it was added 0.2 M sodium bicarbonate pH 8.3 buffer (10 µl) followed by a solution of NH2-6C-4P (15 µmol) in 0.2 M sodium bicarbonate pH 8.3 buffer (50 µl). The resultant solution was stirred overnight and then subjected to reverse-phase HPLC (acetonitrile/0.1 M TEAB gradient) purification to give 0.51 µmol of a product (10% yield) after evaporation of solvent.

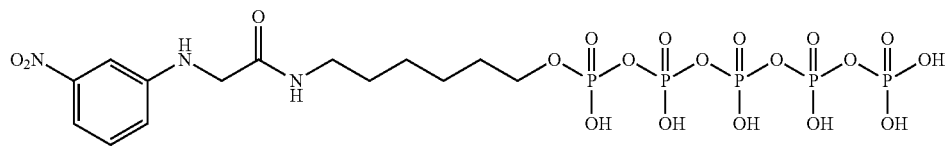

TSQ001-6C-5P

To a solution of TSQ001 (12.8 mg, 43 µmol) in DMF (200 µl) was added excess of carbonyldiimidazole (CDI, 70 mg, 430 µmol) and N-hydroxysuccinimide (NHS, 15 mg, 135 µmol) and stirred for 16 h at ambient temperature. To it was added 0.2 M sodium bicarbonate pH 8.3 buffer (10 µl) followed by a solution of NH2-6C-5P (75 µmol) in 0.2 M sodium bicarbonate pH 8.3 buffer (200 µl). The resultant solution was stirred overnight and then subjected to reverse-phase HPLC (acetonitrile/0.1 M TEAB gradient) purification to give 10.3 mg (8.6 mmol) of a product (20% yield) after evaporation of solvent.

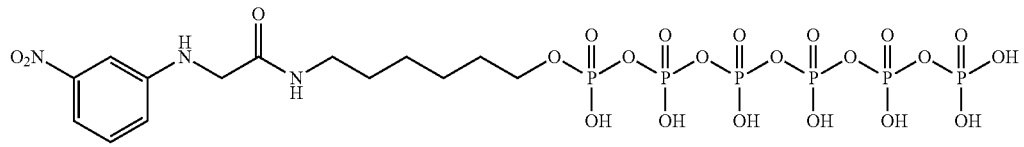

TSQ001-6C-6P

TSQ001 (1.6 mg, 5.4 mmol) in DMF (100 µl) was added excess of carbonyldiimidazole (CDI, 7.0 mg, 43 µmol) and N-hydroxysuccinimide (NHS, 1.5 mg, 14 µmol) and stirred for 16 h at ambient temperature. To it was added 0.2 M sodium bicarbonate pH 8.3 buffer (10 µl) followed by a solution of NH2-6C-6P (11.7 µmol) in 0.2 M sodium bicarbonate pH 8.3 buffer (100 µl). The resultant solution was stirred overnight and then subjected to reverse-phase HPLC (acetonitrile/0.1 M TEAB gradient) purification to give 0.71 µmol of a product (13% yield) after evaporation of solvent.

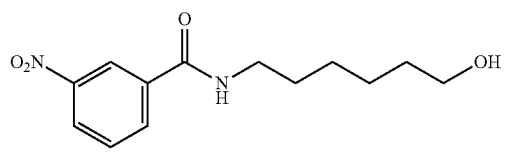

NBA-6C-OH

To a solution of 3-nitrobenzoyl chloride (3.53 g, 19.0 mmol) in 1,4-dioxane (100 mL) and triethylamine (3.18 mL, 22.8 mmol) was added dropwise a solution of 6-aminohexanol (2.675 g, 22.8 mmol) in 1,4-dioxane (20 mL) at 0° C. After stirring overnight the solid was collected through filtration and filtrate was concentrated to also give a solid. The combined solid was then vigorously stirred in acidic water (0.5 M HCl). The solid was collected via filtration and washed with acidic water (3×20 mL) to remove the residual nitrobenzoic acid by-product. The solid was dried under high vacuum in an oven at 45° C. overnight to give 3.43 g of the desired product (67.8% yield).

To a solution of TSQ001 (7.4 mg, 38.1 μmol) in DMF (150 μl) was added excess of carbonyldiimidazole (CDI, 70 mg, 430 μmol) and N-hydroxysuccinimide (NHS, 15 mg, 135 μmol) and stirred for 16 h at ambient temperature. To it was added 0.2 M sodium bicarbonate pH 8.3 buffer (10 μl) followed by a solution of aminocaproic acid NH$_2$C$_5$H$_{10}$COOH (20 mg, 152 μmol) in 0.2 M sodium bicarbonate pH 8.3 buffer (150 μl). The resultant solution was stirred overnight and then subjected to reverse-phase HPLC (acetonitrile/0.1 M TEAB gradient) purification to give 6.1 mg (19.7 μmol) of a product (52% yield) after evaporation of solvent.

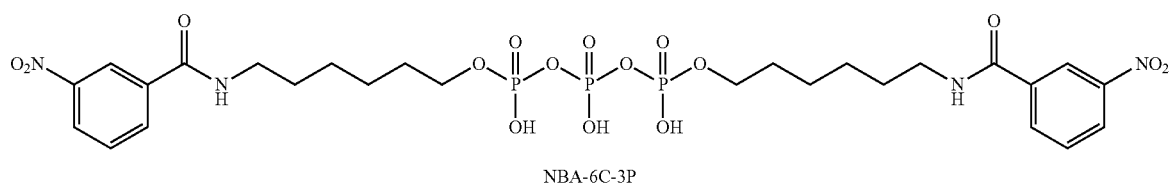 [SMILES: O=C(NCCCCCCOP(=O)(O)OP(=O)(O)OP(=O)(O)OCCCCCCNC(=O)c1cccc([N+](=O)[O-])c1)c1cccc([N+](=O)[O-])c1]

NBA-6C-3P

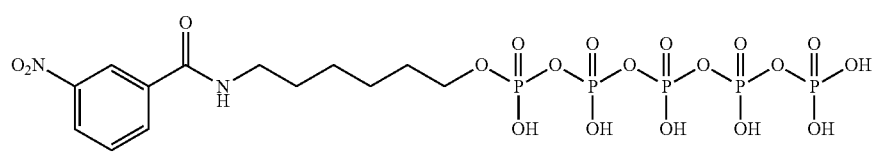

NBA-6C-5P

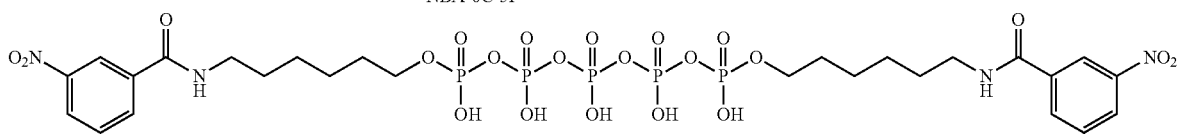

(NBA-6C)2-5P

To a suspension of NBA-6C—OH (73.5 mg, 276 μmol) in methylene chloride (2 mL) and acetonitrile (1 mL), DMF (1 mL) was added phosphorus oxychloride (POCl$_3$, 28.3 μl, 303.6 μmol) under nitrogen atmosphere. After stirring 10 min at 0° C. a solution of tributylammonium pyrophosphate (276 μmol) and triethylamine (276 μmol) in DMF (2 mL) was added dropwise and stirred overnight at ambient temperature. To the solution was added a TEAB buffer (1M, 30 mL) and stirred overnight at ambient temperature. The filtrate was concentrated under reduced pressure to small volume, which was then subjected to ion-exchange and reverse-phase HPLC purification to give the following products: NBA-6C-3P, NBA-6C-4P, NBA-6C-5P, (NBA-6C)2-3P, (NBA-6C)2-4P and (NBA-6C)2-5P, examples of which are shown above.

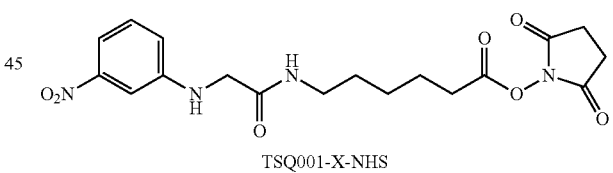

TSQ001-X-NHS

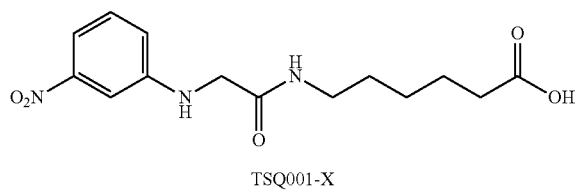

TSQ001-X

To a solution of TSQ001-X (6.1 mg, 19.7 μmol) in DMF (150 μl) was added excess of carbonyldiimidazole (CDI, 13 mg, 80 μmol) and N-hydroxysuccinimide (NHS, 5 mg, 43 μmol) and stirred for 16 h at ambient temperature. To it was added 0.2 M sodium bicarbonate pH 8.3 buffer (10 μl) and then divided into two aliquots (5 μmol and 14 μmol) and used immediately in the following coupling reactions.

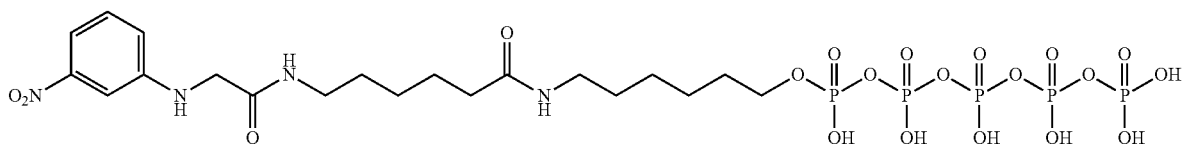

TSQ001-14C-5P

To a solution of TSQ001-X—NHS (5 μmol) in DMF (40 μl) was added a solution of NH2-6C-5P (8 μmol) in 0.2 M sodium bicarbonate pH 8.3 buffer (40 μl). The resultant solution was stirred overnight and then subjected to reverse-phase HPLC (acetonitrile/0.1 M TEAB gradient) purification to give 1.6 μmol of a product (32% yield) after evaporation of solvent.

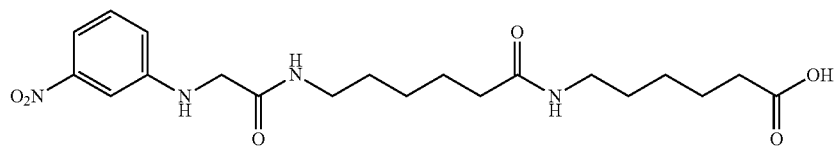

TSQ001-XX

To a solution of TSQ001-X—NHS (14 μmol) in DMF (120 μl) was added a solution of aminocaproic acid $NH_2C_5H_{10}COOH$ (6.6 mg, 50 μmol) in 0.2 M sodium bicarbonate pH 8.3 buffer (75 μl). The resultant solution was stirred overnight and then subjected to reverse-phase HPLC (acetonitrile/0.1 M TEAB gradient) purification to give 3.5 mg (8.3 μmol) of a product (59% yield) after evaporation of solvent.

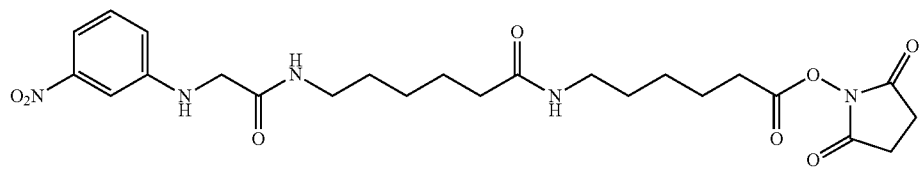

TSQ001-XX-NHS

To a solution of TSQ001-XX (8.3 μmol) in DMF (100 μl) was added excess of carbonyldiimidazole (CDI, 15 mg, 93 μmol) and N-hydroxysuccinimide (NHS, 5 mg, 43 μmol) and stirred for 16 h at ambient temperature. To it was added 0.2 M sodium bicarbonate pH 8.3 buffer (10 μl) and then divided into two aliquots (2.1 μmol and 6.2 μmol) and used immediately in the following coupling reactions.

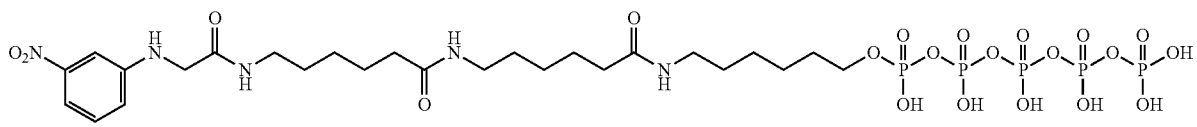

TSQ001-21C-5P

To a solution of TSQ001-XX—NHS (2.1 μmol) in DMF (150 μl) was added a solution of NH2-6C-5P (25 mop in 0.2 M sodium bicarbonate pH 8.3 buffer (150 μl). The resultant solution was stirred overnight and then subjected to reverse-phase HPLC (acetonitrile/0.1 M TEAB gradient) purification to give 0.56 μmol of the desired product (27% yield) after evaporation of solvent.

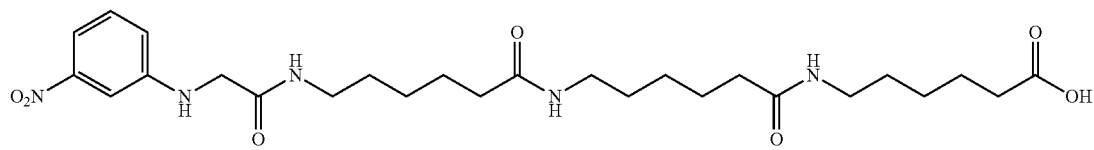

TSQ001-XXX

To a solution of TSQ001-XX—NHS (6.2 mop in DMF (100 μl) was added a solution of aminocaproic acid NH$_2$C$_5$H$_{10}$COOH (6.0 mg, 46 μmol) in 0.2 M sodium bicarbonate pH 8.3 buffer (100 μl). The resultant solution was stirred overnight and then subjected to reverse-phase HPLC (acetonitrile/0.1 M TEAB gradient) purification to give 3.5 μmol (58% yield) the desired product after evaporation of solvent.

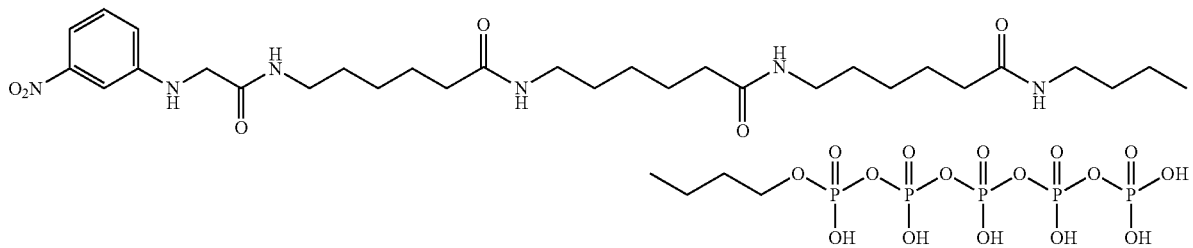

TSQ001-28C-5P

To a solution of TSQ001-XXX (3.5 mop was added excess of carbonyldiimidazole (CDI, 15 mg, 93 μmol) and N-hydroxysuccinimide (NHS, 5 mg, 43 mop and stirred for 16 h at ambient temperature. To it was added 0.2 M sodium bicarbonate pH 8.3 buffer (10 μl) followed by addition of a solution of NH2-6C-5P (17 mop in 0.2 M sodium bicarbonate pH 8.3 buffer (100 μl). The resultant solution was stirred overnight and then subjected to reverse-phase HPLC (acetonitrile/0.1 M TEAB gradient) purification to give 2.59 μmol of the desired product (74% yield) after evaporation of solvent.

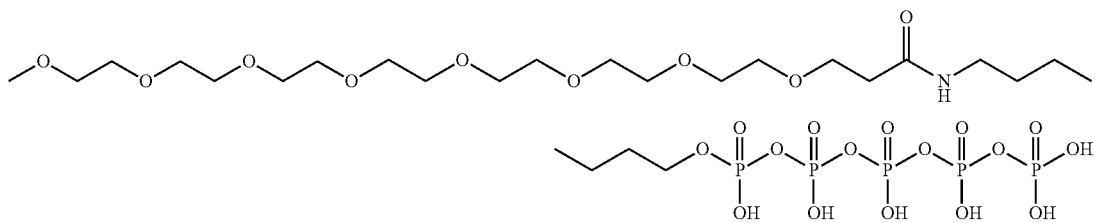

dPEG8-6C-5P

To a solution of m-dPEG8-NHS ester (50.9 mg, 0.10 mmol) in DMF (200 μl) was added a solution of NH$_2$-6C-5P (20 mmol) in 0.2 M sodium bicarbonate pH 8.3 buffer (100 μl). The resultant solution was stirred overnight and then subjected to reverse-phase HPLC (acetonitrile/0.1 M TEAB gradient) purification to give 5.85 mmol of the desired product (29% yield) after evaporation of solvent.

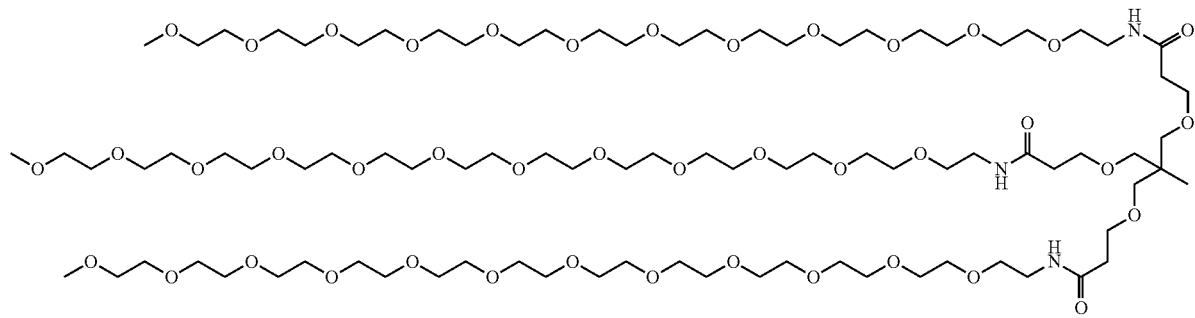

PEG(BR)-6C-5P

To a solution of Branch-(PEG12)$_3$-NHS ester (18.4 mg, 7.6 μmol) in DMF (200 μl) was added a solution of NH2-6C-5P (17 μmol) in 0.2 M sodium bicarbonate pH 8.3 buffer (100 μl). The resultant solution was stirred overnight and then subjected to reverse-phase HPLC (acetonitrile/0.1 M TEAB gradient) purification to give 1.29 mmol of the desired product (greater than 17% yield) after evaporation of solvent.

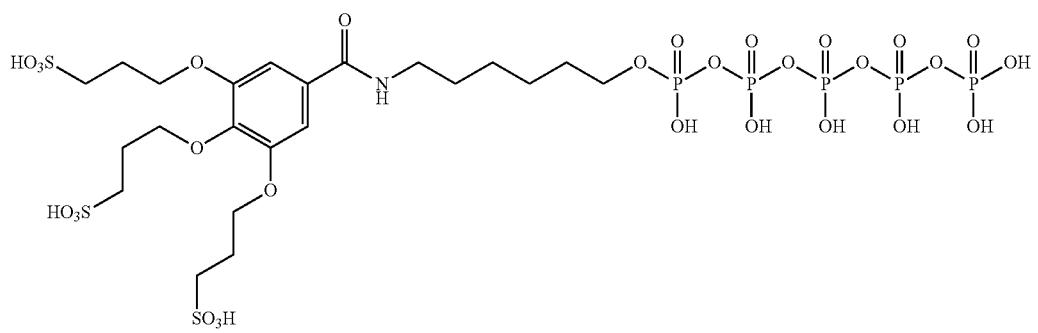

SG1-6C-5P (3,4,5-Trisulfopropyloxybenzoate-6C-5P)

To a solution of 3,4,5-trisulfopropyloxybenzoic acid (6.2 mg, 6.6 μmol) was added excess of carbonyldiimidazole (CDI, 15 mg, 93 μmol) and N-hydroxysuccinimide (NHS, 5 mg, 43 μmol) and stirred for 16 h at ambient temperature. To it was added 0.2 M sodium bicarbonate pH 8.3 buffer (10 μl) followed by addition of a solution of NH2-6C-5P (12 μmol) in 0.2 M sodium bicarbonate pH 8.3 buffer (100 μl). The resultant solution was stirred overnight and then subjected to reverse-phase HPLC (acetonitrile/0.1 M TEAB gradient) purification to give 6.45 μmol (98%) of the desired product after evaporation of solvent.

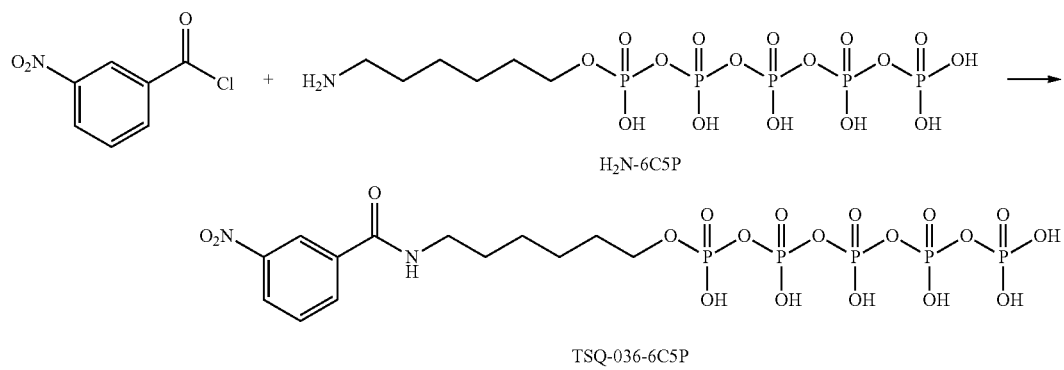

A solution of 3-nitrobenzoyl chloride (53 µmole) in 40 µl dioxane was added to a solution of H$_2$N-6C5P (5.6 µmole) in 100 µl 0.15 N NaHCO$_3$. The reaction was stirred for 30 min. The reaction was diluted with 4 mL 0.1 M TEAB buffer (pH7.0), filtered, and purified by reverse phase HPLC eluted with an increasing gradient of CH$_3$CN over 0.1 N TEAB buffer (pH 7.0). The yield of the product, TSQ-036-6C5P, was 2.6 µmole (46%).

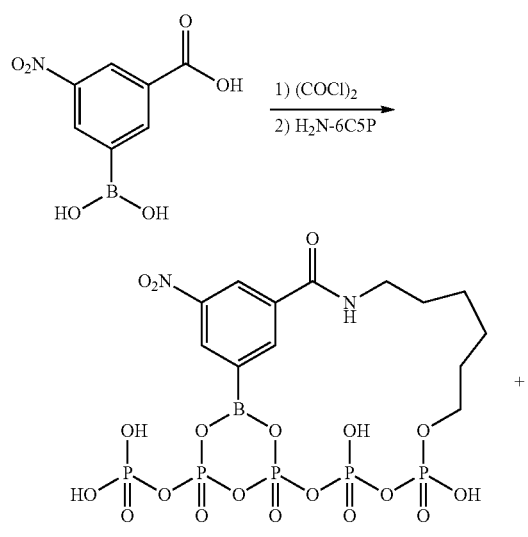

-continued

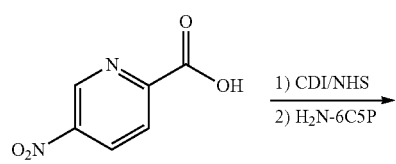

DMF (10 µl) was added to a solution of 3-carboxy-5-nitrophenylboronic acid (49 µmole) in 400 µl of oxalyl chloride in a 10 mL round bottle flask. The reaction was stirred at 25° C. for 2 hr. The oxalyl chloride was removed in vacuo and the residue was dissolved in 100 µl dioxane. A solution of H$_2$N-6C5P (5.6 µmole) in 200 µl 0.1 N NaHCO$_3$ was added to the dioxane solution, the reaction stirred for 1 hr. The reaction was diluted with 4 mL 0.1 M TEAB buffer (pH 7.0), filtered, and purified by reverse phase HPLC eluted with an increasing gradient of CH$_3$CN over 0.1 N TEAB buffer. The yield of the product, TSQ-035-6C5P, was 1.4 µmole (25%).

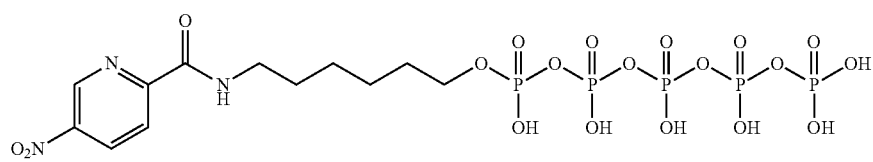

Carbonyldiimidazole (CDI, 66 μmole) and N-hydroxysuccinimide (NHS, 70 μmole) was added to a solution of 5-nitropicolinic acid (58 μmole) in 200 μl of DMA. The reaction was stirred at 25° C. for 16 hr. A solution of H$_2$N-6C5P (5.6 μmole) in 200 μl 0.1 N NaHCO$_3$ was added to the reaction, stirred for another 1 hr. The reaction was diluted with 4 mL 0.1 M TEAB buffer (pH 7.0), filtered, and purified by reverse phase HPLC eluted with an increasing gradient of CH$_3$CN over 0.1 N TEAB buffer. The yield of the product, TSQ-032-6C5P, was 4.8 μmole (85%).

Although described in some detail for purposes of illustration, it will be readily apparent that a number of variations or modifications known or appreciated by those of skill in the art may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. For example, in certain embodiments various compounds described herein can be combined within a single reaction mixture, in particular where their modes of action differ and/or complement one another. Unless otherwise clear from the context or expressly stated, any concentration values provided herein are generally given in terms of admixture values or percentages without regard to any conversion that occurs upon or following addition of the particular component of the mixture. All publications mentioned herein are cited for the purpose of describing and disclosing reagents, methodologies and concepts that may be used in connection with the present invention. Nothing herein is to be construed as an admission that these references are prior art in relation to the inventions described herein. To the extent not already expressly incorporated herein, all published references and patent documents referred to in this disclosure are incorporated herein by reference in their entirety for all purposes.

What is claimed is:

1. A reaction mixture comprising a first reactant, a second reactant comprising a fluorescent or fluorogenic label, and an additive, the additive comprising:
   a first photoprotective moiety linked to a polyanion moiety through a first linker, the first linker comprising at least one methylene group; and
   a second photoprotective moiety linked to the polyanion moiety;
   wherein the additive reduces an amount of photo-induced damage to the first reactant caused by interaction of the first and second reactants under excitation illumination.

2. The reaction mixture of claim 1, wherein the first reactant is an enzyme selected from the group consisting of a polymerase, ribosome, helicase, nuclease, and ligase enzyme.

3. The reaction mixture of claim 1, further comprising a template nucleic acid molecule.

4. The reaction mixture of claim 1, wherein the second reactant comprises a nucleoside polyphosphate, tRNA, or analog thereof.

5. The reaction mixture of claim 1, wherein at least one component of the reaction mixture is confined within a zero-mode waveguide.

6. The reaction mixture of claim 1, wherein the additive is present at a concentration between 0.5 and 10 μM.

7. The reaction mixture of claim 1, wherein the first photoprotective moiety comprises a nitrobenzene derivative.

8. The reaction mixture of claim 1, wherein the polyanion moiety comprises at least three to six phosphate groups, sulfonate groups, phosphonate groups, arsonate groups, and carboxy groups.

9. The reaction mixture of claim 1, wherein the additive has the formula:

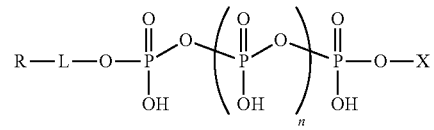

wherein
   R is the first photoprotective moiety;
   L is the first linker;
   n is selected from 1, 2, 3, 4, 5 and 6; and
   X is L'-R', wherein
      L' is a second linker; and
      R' is the second photoprotective moiety.

10. The reaction mixture of claim 9, wherein R' is a substituted or unsubstituted aryl moiety.

11. The reaction mixture of claim 1, wherein the first and second photoprotective moiety are members independently selected from:

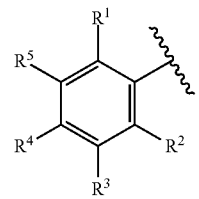

wherein
   R$^1$, R$^2$, R$^3$, R$^4$, and R$^5$ are independently members selected from H, substituted or unsubstituted alkyl, substituted or unsubstituted heteroalkyl, substituted or unsubstituted aryl, substituted or unsubstituted heteroaryl, halogen, CN, CF$_3$, acyl, —SO$_2$NR$^6$R$^7$, —NR$^6$R$^7$, —OR$^6$, —S(O)$_2$R$^6$, —C(O)R$^6$, —COOR$^6$, —CONR$^6$R$^7$, —S(O)$_2$OR$^6$, —OC(O)R$^6$, —C(O)NR$^6$R$^7$, —NR$^6$C(O)R$^7$, —NR$^6$SO$_2$R$^7$ and —NO$_2$, wherein two or more of R$^1$, R$^2$, R$^3$, R$^4$ and R$^5$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl
wherein
   R$^6$ and R$^7$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and R$^6$ and R$^7$, together with the atoms to which they are bonded, are optionally joined to form a 5-to 7-membered ring which is a member selected from substituted or unsubstituted cycloalkyl, substituted or unsubstituted heterocycloalkyl, substituted or unsubstituted aryl and substituted or unsubstituted heteroaryl.

12. The reaction mixture of claim 11, wherein at least one of $R^1$, $R^2$, $R^3$, $R^4$, and $R^5$ is $NO_2$.

13. A method for protecting an enzyme from photo-induced damage in an illuminated reaction, the method comprising:
providing a reaction mixture comprising the enzyme, and a fluorescent or fluorogenic substrate for the enzyme, wherein interaction of the enzyme and the fluorescent or fluorogenic substrate under excitation illumination results in altered activity of the enzyme;
adding an additive to the reaction mixture, the additive comprising;
a first photoprotective moiety linked to a polyanion moiety through a first linker, the first linker comprising at least one methylene group; and
a second photoprotective moiety linked to the polyanion moiety; and
illuminating the reaction mixture with an excitation illumination, wherein the additive reduces an amount of photo-induced damage to the enzyme resulting from interaction of the enzyme with the fluorescent or fluorogenic substrate under the excitation illumination to an amount that is less than that which would occur in the absence of the additive.

14. The method of claim 13, wherein the enzyme is a polymerase or a ligase.

15. The method of claim 13, wherein the reaction mixture further comprises a template nucleic acid molecule, and further wherein the fluorescent or fluorogenic substrate comprises a nucleoside polyphosphate or analog thereof.

16. The method of claim 13, wherein at least one component of the reaction mixture is confined within a zero-mode waveguide.

17. The method of claim 13, wherein the first photoprotective moiety comprises a nitrobenzene derivative.

18. The method of claim 13, wherein the additive is present at a concentration between 0.5 and 10 μM.

19. The method of claim 13, wherein the polyanion moiety comprises at least three to six anion moieties selected from the group consisting of phosphate groups, sulfonate groups, phosphonate groups, arsonate groups, and carboxy groups.

20. The method of claim 13, wherein the additive has the formula:

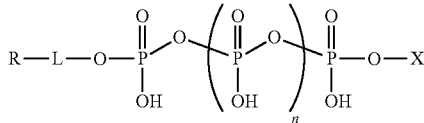

wherein
R is the first photoprotective moiety;
L is the first linker;
n is selected from 1, 2, 3, 4, 5 and 6; and
X is L'-R', wherein
L' is a second linker; and
R' is the second photoprotective moiety.

21. A compound having the formula:

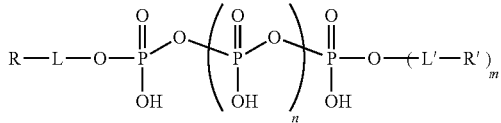

in which
R and R' are independently selected photoprotective moieties;
L and L' are linkers independently selected alkyl linkers;
n is selected from 1, 2, 3, 4, 5 and 6; and
m is 1.

22. The compound of claim 21, wherein R and R' are members independently selected from:

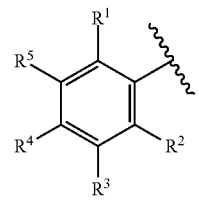

wherein
$R^1$, $R^2$, $R^3$, $R^4$, and $R^5$ are independently members selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^6R^7$, $-NR^6R^7$, $-OR^6$, $-S(O)_2R^6$, $-C(O)R^6$, $-COOR^6$, $-CONR^6R^7$, $-S(O)_2OR^6$, $-OC(O)R^6$, $-C(O)NR^6R^7$, $-NR^6C(O)R^7$, $-NR^6SO_2R^7$ and $-NO_2$, wherein two or more of $R^1$, $R^2$, $R^3$, $R^4$ and $R^5$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl wherein
$R^6$ and $R^7$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^6$ and $R^7$, together with the atoms to which they are bonded, are optionally joined to form a 5-to 7-membered ring which is a member selected from substituted or unsubstituted cycloalkyl, substituted or unsubstituted heterocycloalkyl, substituted or unsubstituted aryl and substituted or unsubstituted heteroaryl.

23. The compound of claim 22, wherein at least one of $R^1$, $R^2$, $R^3$, $R^4$, and $R^5$ is $NO_2$.

24. The compound of claim 21, wherein R and R' are members independently selected from the formula:

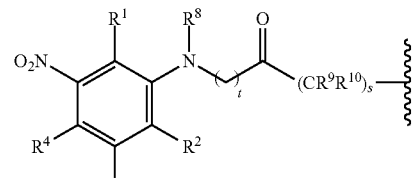

wherein
$R^8$ is selected from H and substituted or unsubstituted alkyl;

$R^9$ and $R^{10}$ are independently selected from from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^{11}R^{12}$, $-NR^{11}R^{12}$, $-OR^{11}$, $-S(O)_2R^{11}$, $-C(O)R^{11}$, $-COOR^{11}$, $-CONR^{11}R^{12}$, $-S(O)_2OR^{11}$, $-OC(O)R^{11}$, $-C(O)NR^{11}R^{12}$, $-NR^{11}C(O)R^{12}$, $-NR^{11}SO_2R^{12}$ and $-NO_2$, wherein $R^{11}$ and $R^{12}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^6$ and $R^7$, together with the atoms to which they are bonded, are optionally joined to form a 5-to 7-membered ring which is a member selected from substituted or unsubstituted cycloalkyl, substituted or unsubstituted heterocycloalkyl, substituted or unsubstituted aryl and substituted or unsubstituted heteroaryl; and s and t are independently selected from 0, 1, 2, 3, 4, 5, 6; 7, 8, 9 and 10.

25. The method of claim 20, wherein R' is a substituted or unsubstituted aryl moiety.

\* \* \* \* \*